United States Patent [19]

Soudijn et al.

[11] 4,031,226

[45] June 21, 1977

[54] N-[(1-PIPERIDINYL)ALKYL]ARYLCARBOXAMIDE DERIVATIVES

[75] Inventors: Willem Soudijn; Ineke van Wijngaarden, both of Oud-Turnhout; Paul Adriaan Jan Janssen, Vosselaar, all of Belgium

[73] Assignee: Janssen Pharmaceutica N.V., Beerse, Belgium

[22] Filed: June 21, 1976

[21] Appl. No.: 697,813

Related U.S. Application Data

[63] Continuation-in-part of Ser. No. 604,282, Aug. 13, 1975, abandoned.

[52] U.S. Cl. .............................. 424/267; 260/293.6; 260/293.66; 260/293.67; 260/293.68; 260/293.69; 260/293.71; 260/293.77; 260/293.78; 424/263

[51] Int. Cl.$^2$ ............. C07D 211/52; C07D 401/04

[58] Field of Search ..... 260/293.6, 293.66, 293.67, 260/293.68, 293.69, 293.71, 293.77, 293.78; 424/263, 267

[56] References Cited

UNITED STATES PATENTS 3,342,826   9/1967   Miller et al. .................... 260/294

FOREIGN PATENTS OR APPLICATIONS 620,543   11/1962   Belgium
5,819M    4/1968    France

*Primary Examiner*—G. Thomas Todd
*Attorney, Agent, or Firm*—Salvatore R. Conte

[57] ABSTRACT

Compounds of the class of N-[(1-piperidinyl)alkyl]arylcarboxamides, useful as antiemetic and psychotropic agents.

16 Claims, No Drawings

4,031,226

N-[(1-PIPERIDINYL)ALKYL]ARYLCARBOXA-MIDE DERIVATIVES

CROSS-REFERENCE TO RELATED APPLICATIONS

This is a continuation-in-part of our copending application Ser. No. 604,282, filed Aug. 13, 1975 now abandoned.

BACKGROUND OF THE INVENTION

In the literature there may be found some N-[(dialkylamino)-alkyl]benzamides, including N-[(1-piperidinyl)alkyl]benzamides; and some N-[(2-pyrrolidinyl)methyl]benzamides having pharmacological properties. Well-known specific examples of such prior art compounds are 4-amino-5-chloro-N-[2-(diethylamino)ethyl]-2-methoxybenzamide, generically designated as metoclopramide and used as an antiemetic agent; and 5-aminosulfonyl-N-[(1-ethyl-2-pyrrolidinyl)methyl]-2-methoxybenzamide, generically designated as sulpiride and used as an antiemetic and neuroleptic agent.

Among other points of difference the compounds of this invention differ from those of the prior art by the nature of the substituted piperidine nucleus attached to the alkyl side-chain. A number of such prior art compounds may be found in the following references:
C.A. 59, 11358c;
U.S. Pat. No. 3,342,826; and
C.A., 71, P81413c.

DESCRIPTION OF THE PREFERRED EMBODIMENTS

The novel N-[(1-piperidinyl)alkyl]arylcarboxamide derivatives of this invention may structurally be represented by the following formula:

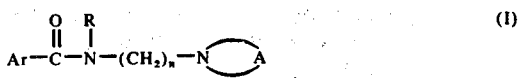

and the pharmaceutically acceptable acid addition salts thereof, wherein:

Ar is an aryl radical selected from the group consisting of phenyl, substituted phenyl, 2-thienyl, 2-furanyl, pyridinyl and 1-methyl-2-pyrrolyl, wherein said substituted phenyl is phenyl having from 1 to 3 substituents independently selected from the group consisting of halo, lower alkyl, lower alkyloxy, trifluoromethyl, nitro, hydroxy, amino, lower alkylcarbonyloxy and lower alkylcarbonylamino, provided that when more than 1 of said substituents are present only one thereof may be selected from the group consisting of hydroxy, amino, lower alkylcarbonyloxy and lower alkylcarbonylamino;

R is a member selected from the group consisting of hydrogen and lower alkyl;

$n$ is an integer from 2 to 3 inclusive; and the radical

is a member selected from the group consisting of
a. a radical having the formula:

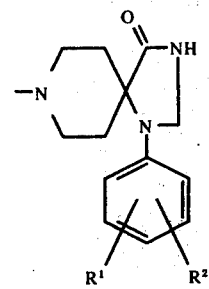

wherein $R^1$ and $R^2$ are each independently selected from the group consisting of hydrogen, halo, lower alkyl and trifluoromethyl;

b. a radical having the formula:

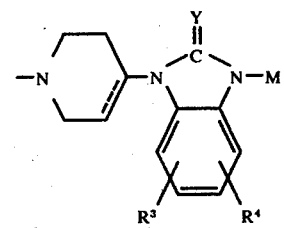

wherein $R^3$ and $R^4$ are each independently selected from the group consisting of hydrogen, halo, lower alkyl and trifluoromethyl; M is selected from the group consisting of hydrogen, lower alkyl, lower alkylcarbonyl and 2-cyanoethyl; Y is selected from the group consisting of O, S and lower alkylcarbonylimino; and the dotted line indicates that the double bond between the 3- and 4-carbon atoms of the piperidine nucleus is optional, provided that when there is a double bond between said 3- and 4-carbon atoms, then said Y is O and said M is hydrogen.

c. a radical having the formula:

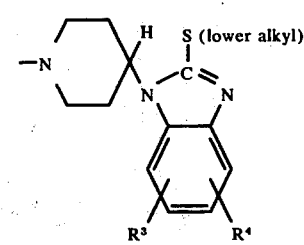

wherein $R^3$ and $R^4$ are each independently selected from the group consisting of hydrogen, halo, lower alkyl and trifluoromethyl; and d. a radical having the formula:

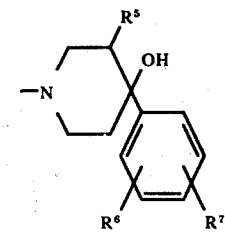

wherein $R^5$ is selected from the group consisting of hydrogen and methyl; $R^6$ is selected from the group consisting of hydrogen and halo; and $R^7$ is selected from the group consisting of hydrogen, halo, lower alkyl and trifluoromethyl.

As used herein "lower alkyl" may be straight or branch chained and have from 1 to about 5 carbon atoms, such as, for example, methyl, ethyl, propyl, 1-methylethyl, butyl, pentyl and the like; and the term "halo" is generic to halogens of atomic weight less than 127, i.e., fluoro, chloro, bromo and iodo.

Compounds of formula (I) wherein Ar and

are as previously defined, R is hydogen and $n$ is 2, (i-a), may generally be prepared by reacting an appropriately substituted 1-aroylaziridine of the formula (II), wherein Ar has the previously indicated meaning, with an appropriate piperidine derivative of formula (III) wherein the

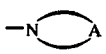

group is as previously defined.

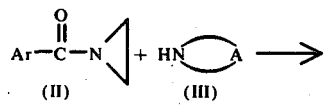

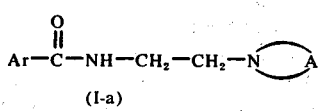

(I-a)

The foregoing reaction is preferably carried out in an appropriate reaction-inert organic solvent, such as, for example, a lower alkanol, e.g. methanol, ethanol, propanol, butanol and the like alcohols; an aromatic hydrocarbon, e.g., benzene, methylbenzene, dimethylbenzene and the like; a ketone, e.g., 4-methyl-2-pentanone; an ether, e.g., 1,4-dioxane, 1,1'-oxybisethane and the like; N,N-dimethylformamide; nitrobenzene, and the like; or a mixture of such solvents. Elevated temperatures are appropriate in order to enhance the rate of the reaction and preferably the reaction is carried out at the reflux temperature of the reaction mixture.

In this and following procedures the reaction products are separated from the medium and, if necessary, further purified by the application of methodologies known in the art.

The compounds of formula (I), including those wherein R is lower alkyl and those wherein $n$ is 3 may also be prepared by the reaction of a suitable reactive ester of formula (IV) wherein Ar, R and $n$ are as previously defined and X is an appropriate reactive ester function derived from the corresponding alcohol, such as, for example, halo, methanesulfonyl, 4-methylbenzenesulfonyl and the like, with an appropriate piperidine derivative of formula (III).

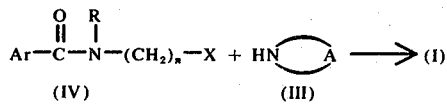

The foregoing reaction is preferably carried out in a suitable organic solvent such as, for example, N,N-dimethylformamide, N,N-dimethylacetamide, 4-methyl-2-pentanone, 2-propanol, methanol, ethanol, 2-propanone and the like solvents. The additions of an appropriate base, e.g., an alkali metal or earth alkali metal carbonate or hydrogen carbonate may be utilized to pick up the acid that is liberated during the course of the reaction. Somewhat elevated temperatures are appropriate to enhance the reaction rate and preferably the reaction is carried out at reflux temperature.

Still another method of preparing the compounds of formula (I) consists in reacting an appropriately substituted aroyl halide of formula (V) with an appropriate amine of formula (VI) according to methodologies generally known in the art for the preparation of amides starting from an aryl halide and an amine.

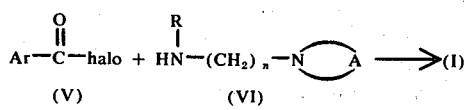

For example, the foregoing reaction may conveniently be carried out by refluxing the reactants together in a suitable reaction-inert organic solvent, such as, for example, a lower alkanol, e.g., methanol, ethanol, propanol, butanol and the like alcohols; an aromatic hydrocarbon, e.g. benzene, methylbenzene, dimethylbenzene, and the like; a ketone, e.g., 4-methyl-2-pentanone; an ether, e.g., 1,4-dioxane, 1,1'-oxybisethane and the like; N,N-dimethylformamide; nitrobenzene; and the like; or a mixture of such solvents. Elevated temperatures are appropriate to enhance the rate of the reaction and preferably the reaction is carried out at the reflux temperature of the reaction mixture.

The compounds of formula (I) wherein Ar is a phenyl group having thereon an amino group, alone or together with other substituents, may still be prepared by subjecting the corresponding nitro-subtituted analogs to a nitro-to-amine reduction reaction according to known procedures, e.g., by catalytic hydrogenation using, for example, Raney nickel, palladium-on-charcoal or platinium dioxide catalyst or by the treatment of nitro compounds with iron-ammonium chloride or zinc acetic acid.

Compounds of formula (I) wherein Ar is a phenyl group having thereon a lower alkylcarbonylamino or lower alkylcarbonyloxy can easily be derived from respectively the corresponding amino or hydroxy substituted analogs by acylating the latter with an appropriate acylating agent such as, for example a halide or anhydride derived from the appropriate lower alkylcarboxylic acid. The acylation reaction may, e.g., conveniently be carried out by using an appropriate lower alkylcarboxylic acid anhydride in water.

Compounds of formula (I) which may be represented by the formula:

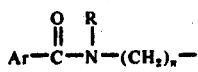

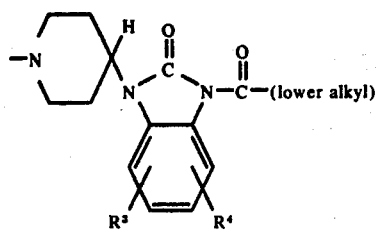
(I-b)

can similarly be prepared starting from a corresponding unsubstituted compound of the formula:

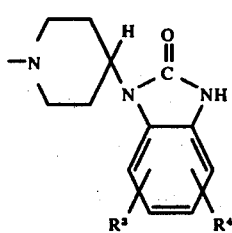
(I-C)

by acylating the latter with an appropriate acylating agent derived from the appropriate lower alkylcarboxylic acid, e.g., an acyl halide or anhydride. For example, said acylation reaction may conveniently be carried out by using an appropriate anhydride in a suitable organic solvent, such as, for example, benzene, methylbenzene, dimethylbenzene and the like.

Compounds of formula (I) which may be represented by the formula:

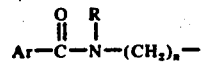

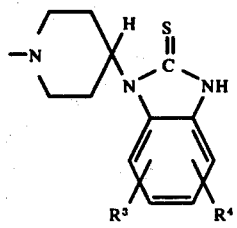
(I-d)

may also be prepared by subjecting an appropriate diamine of the formula:

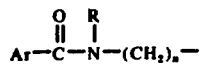

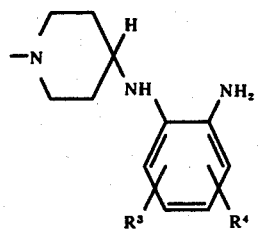
(VII)

to ring closure with an appropriate sulfur containing cyclizing agent such as, for example carbon disulfide, thiourea, carbonothioic dichloride, ammonium thiocyanate and the like.

Compounds of formula (I) which may be represented by the formula:

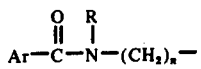

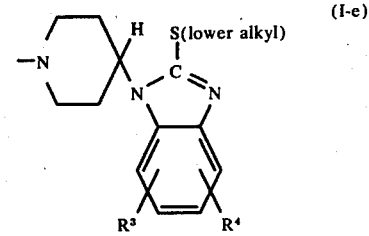
(I-e)

may still be prepared starting from a corresponding compound of formula (I–d), by S-alkylation of the latter according to standard S-alkylating procedures, e.g., by the reaction of (I–d) with an appropriate halo-lower alkane or with an appropriate di(lower alkyl) sulfate.

The starting materials used in the foregoing preparations may be obtained following the procedures indicated hereinafter.

The aroylaziridine intermediates of formula (II), a number of which are known compounds, can easily be prepared by the application of art-known procedures as described in the literature, e.g., by the reaction of an aroyl halide of formula (V) with aziridine (VIII) in the presence of an appropriate base to neutralize any acid which is liberated during the course of the reaction,. The reaction is carried out in an appropriate solvent system, such as, for example, a mixture of water and trichloromethane. The foregoing reaction may be illustrated as follows.

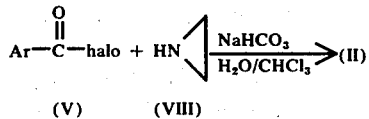

The intermediates of formula (IV), some of which are also described in the literature, may conveniently be prepared, for example, by the N-aroylation of an appropriate aminoalkanol of formula (IX) with an appropriate aroyl halide (V) or with an appropriate lower alkylarylcarboxylate formula (X) according to standard N-aroylating procedures, followed by the conversion of the hydroxyl group on the alkyl side chain of the thus obtained (XI) into a reactive ester group following well-known procedures.

In the preparation of halides there may be used common halogenating agents, such as, for example, carbonic dichloride, sulfinyl chloride, sulfuryl chloride, phosphor pentachloride, phosphor pentabromide, phosphoryl chloride and the like. When the reactive ester is an iodide it is preferably from the corresponding chloride or bromide by the replacement of that halogen with iodine. Other reactive esters such as methanesulfonates and 4-methylbenzenesulfonates are obtained by the reaction of the alcohol with an appropriate sulfonyl halide, such as, for example, methanesulfonyl chloride and 4-methylbenzenesulfonyl chloride respectively. The foregoing reactions are illustrated in the following schematic representation.

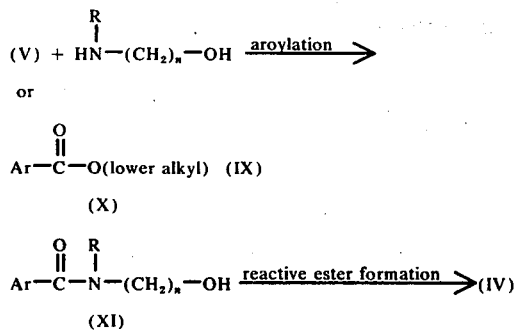

The intermediates of formula (IV) wherein X is halo, (IV-a) may alternatively be obtained in one step by the reaction of an appropriate aroyl halide (V) with an appropriate halo-alkanamine (XII) in an appropriate solvent, such as, for example, N,N-dimethylformamide (DMF), and N,N-dimethylacetamide, preferably in the presence of an appropriate base, such as, for example, N,N-diethylethanamine.

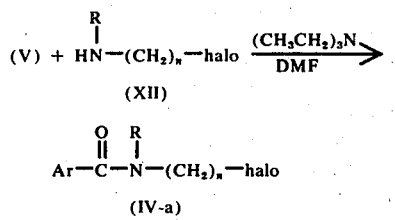

By carrying out the foregoing reaction in alkaline medium and using an intermediate of formula (XII) wherein R is hydrogen and n is 2, the corresponding aziridines of formula (II) may be obtained.

The intermediates of formula (VI) may be prepared as follows. An appropriate lower alkyl N-(haloalkyl)-carbamate of formula (XIII) is reacted with an appropiate piperidine derivative of formula (III) according to common N-alkylating procedures, e.g., by heating the reactants together in an appropriate reaction-inert organic solvent, such as, for example, a lower alkanol, e.g., methanol, ethanol and the like, whereupon there is obtained a carbamate of formula (XIV). The latter is then subjected to acid or alkaline hydrolysis whereupon decarboxylation occurs, yielding the desired intermediates of formula (VI).

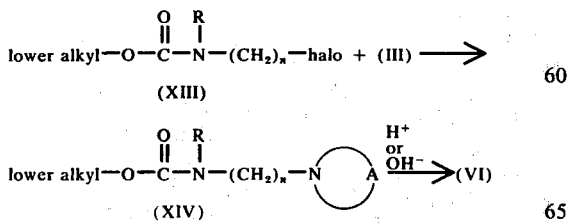

In carrying out alkaline hydrolysis, metal bases, such as, sodium and potassium hydroxide may advantageously be employed. Acids to be used in acid hydrolysis include strong mineral acids such as hydrochloric, hydrobromic, sulfuric, phosphoric acid and the like.

When

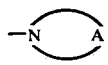

in the intermediate (VI) has the formula

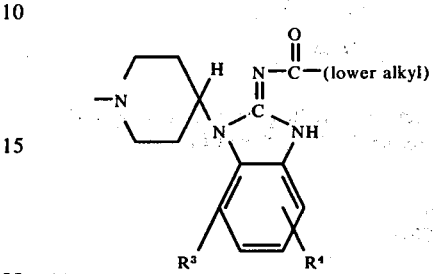

it is appropriate to use instead of (XIII) the corresponding phenylmethyl carbamate, in which case the subsequent decarboxylation may be performed by catalytic hydrogenation using an appropriate catalyst, e.g., palladium-on-charcoal.

The intermediates of formula (VI) are deemed to be novel and as useful intermediates in the preparation of the compounds of formula (I) they constitute an additional feature of this invention.

Intermediates of formula (VII) are conveniently prepared by introducing the aroylaminoalkyl chain into a N-(2-nitrophenyl)-4-piperidinamine of formula (XV) by reacting the latter with an aziridine of formula (II) or reactive ester of formula (IV), and subsequent reduction of the nitro group of the thus obtained (XVI) following standard nitro-to-amine reduction procedures as previously described herein.

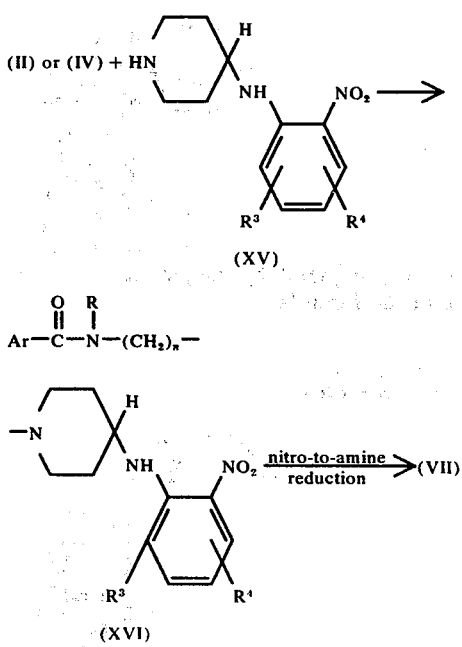

Starting materials of formula (III), represented by the formulas:

a) 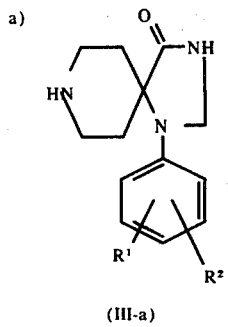

(III-a)

b) 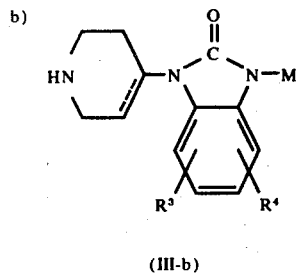

(III-b)

c) 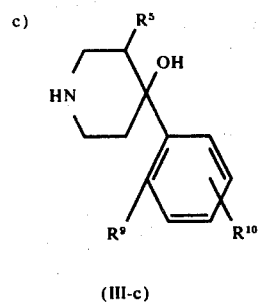

(III-c)

and methods of preparing the same may be respectively be found in the following references:
a. U.S. Pat. No. 3,238,216;
b. U.S. Pat. No. 3,161,645; Belg. Pat. No. 830, 403;
c. U.S. Pat. No. 3,518,276; and U.S. Pat. No. 3,575,990.

Starting materials of formula (III) which are represented by the formulas:

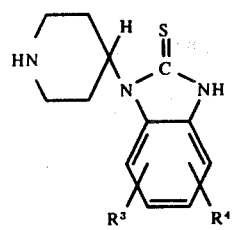

(III-d)

and

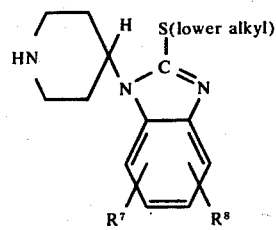

(III-e)

may generally be prepared starting from an appropriate N-(2-aminophenyl)-4-piperidinamine of the formula:

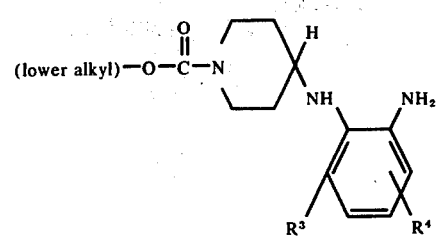

(XVII)

The starting materials (III-d) are conveniently prepared by the cyclization of (XVII) with an appropriate cyclizing agent, e.g., carbon disulfide and subsequent removal of the lower alkyloxycarbonyl group of the thus obtained (XVIII) by alkaline hydrolysis.

The starting materials (III-e) can be prepared by S-alkylating (XVIII) as described hereinabove for the preparation of (I-e) starting from (I-d) followed by elimination of the lower alkyloxycarbonyl group of the resulting (XIX).

The N-(2-aminophenyl)-4-piperidinamines of formula (XVII), a number of which are known compounds, may be prepared following the procedures outlines in U.S. Pat. No. 3,910,930 and Belg. Pat. No. 830,403.

The foregoing procedures are illustrated in the following schematic representation.

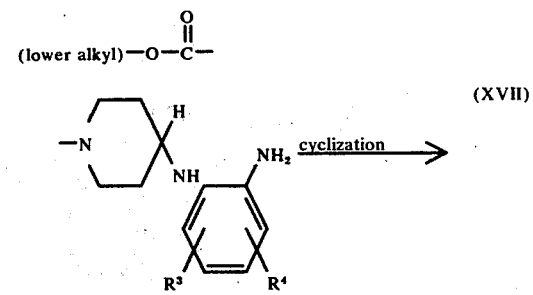

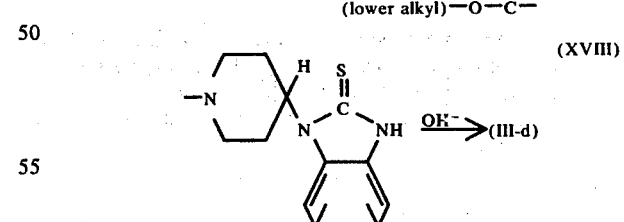

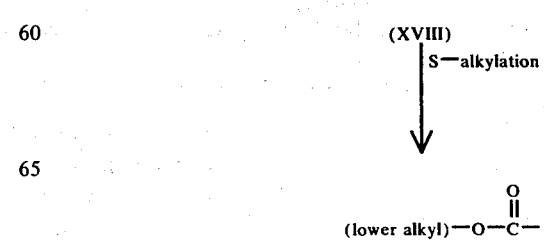

-continued

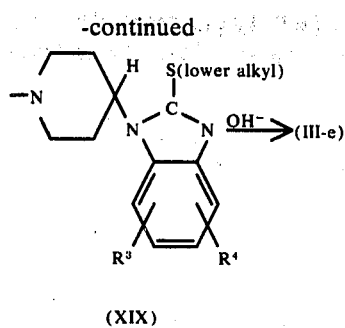

(XIX)

The intermediates of formula (III) which are represented by the formula:

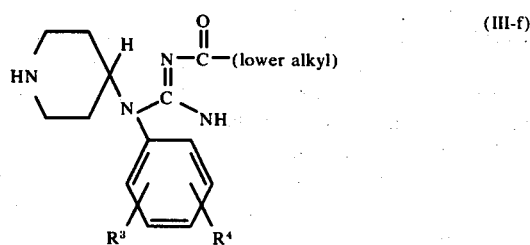

can be prepared as follows.

An appropriate N-(2-aminophenyl)-1-(phenylmethyl)-4-piperidinamine of formula (XX) is converted into the corresponding 1-[1-(phenylmethyl)-4-piperdinyl]-1H-benzimidazol-2-amine (XXI) by the cyclization of (XX) with an appropriate cyclizing agent as known in the art, e.g., cyanamide. The thus obtained (XXI) is then N-acylated with an appropriate acylating agent derived from the appropriate lower alkylcarboxylic acid, e.g. a halide or anhydride to obtain an intermediate of formula (XXII). The desired (III-f) are then conveniently obtained by eliminating the phenylmethyl group of (XXII) by catalytic hydrogenation using an appropriate catalyst such as, for example, palladium-on-charcoal.

The intermediates (XXI) may also be prepared by converting (XX) into a lower alkyl {1,3-dihydro-1-[1-(phenylmethyl)-4-piperidinyl]-2H-benzimidazol-2-ylidene}carbamate (XXIV) by cyclizing (XX) with an appropriate cyclizing agent as known in the art for the preparation of 2-benzimidazolecarbamates starting from 1,2-benzenediamines, e.g. with a lower alkyl-(iminomethoxymethyl)carbamate of formula (XXIII), and thereafter decarboxylating the latter by acid hydrolysis.

The foregoing reactions are illustrated in the following schematic representation.

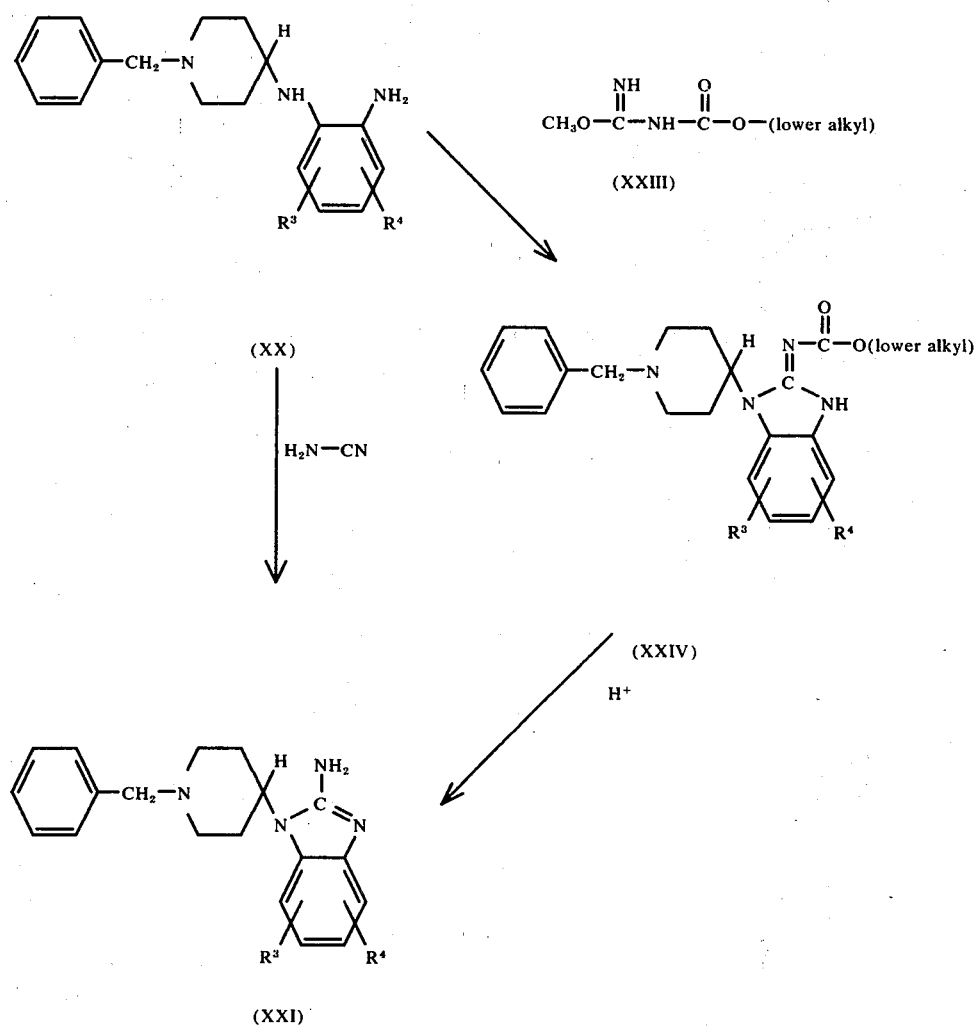

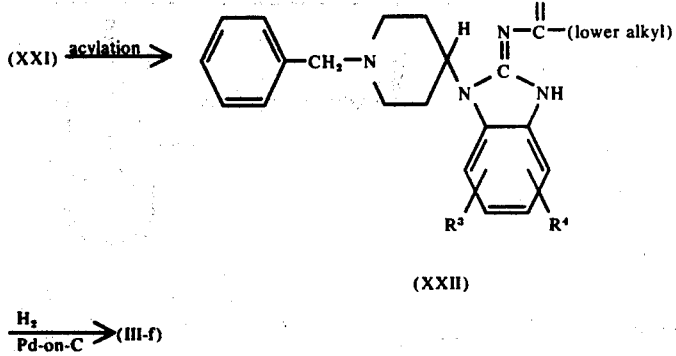

Starting materials of formula (XX) herein may conveniently be obtained by the application of art-known procedures, such as, for example, by the condensation of 1-(phenylmethyl)-4-piperidinamine with an appropriate 2-halo-nitrobenzene of formula (XXV) followed by the reduction of the nitro group of the thus obtained (XXVI) by catalytic hydrogenation using an appropriate catalyst such as, for example, Raney-nickel.

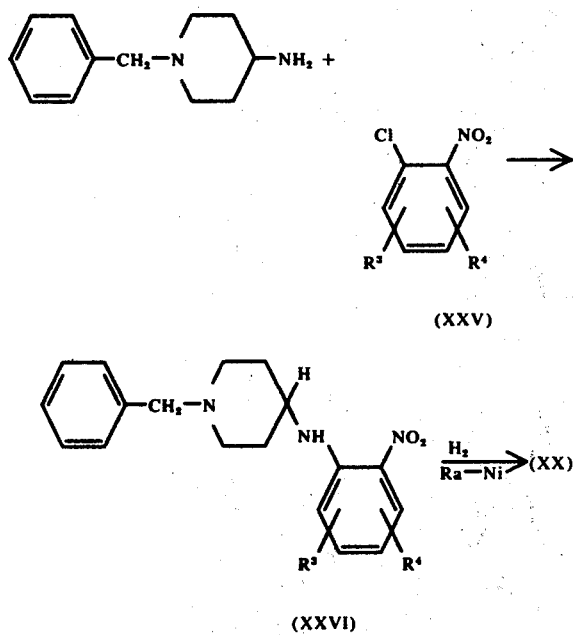

The ultimate starting materials in all of the foregoing procedures are generally known and may be prepared according to art-known procedures.

It is obvious that the compounds of formula (I) wherein

has the formula (III-c) and wherein $R^5$ stands for methyl have two asymmetric carbon atoms within their structure and consequently such compounds may exist under different stereochemically and optically isomeric forms.

Depending on the relative position of the methyl and the hydroxy group with respect to the plane of the piperidine nucleus the compounds have the cis or trans configuration and each of these forms further includes two optical isomers. The stereochemical and optical isomers of these compounds, which are naturally intended to be within the scope of this invention, may be prepared following methodologies known to those skilled in the art. Cis and trans isomers of such compounds and of precursors therefor may be obtained separately by physical methods, e.g., selective crystallization. Without further reference to their actual stereochemical configuration, the form which is first isolated is herein referred to as the A-form and the remaining as the B-form. Since the compounds involved have basic properties, optically active acids may be employed in the resolution of the racemic cis and trans forms to obtain the optical isomers thereof.

The compounds of this invention may be converted to their therapeutically useful acid addition salts by treatment with an appropriate acid, such as, for example, an inorganic acid, such as hydrohalic acid, e.g., hydrochloric, hydrobromic and the like, and sulfuric acid, nitric acid, phosphoric acid and the like; or an organic acid, such as, for example, acetic, propanoic, 2-hydroxyacetic, 2-hydroxypropanoic, 2-oxopropanoic, propanedioic, butanedioic, (Z)-2-butenedioic (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) and the therapeutically active acid addition salts thereof have been found to possess strong antiemetic activity as is evidenced by their ability to block apomorphine-induced vomiting in dogs. The method used is described previously by P. A. J. Janssen and C. J. E. Niemegeers in: Arzneim. -Forsch. (Drug Res), 9, 765–767 (1959).

The compounds listed below were administered subcutaneously to beagle dogs at different doses and the animals were challenged 1 hour thereafter with a standard dose of 0.31 mg/kg (subcutaneous) of apomorphine.

The tables below give the $ED_{50}$ values of a number of the compounds under consideration. As used herein, the $ED_{50}$ value represents the dose which protects 50% of the animals from emesis.

It is understood that the compounds shown in the tables are not listed for the purpose of limiting the invention thereto, but only to exemplify the outstanding antiemetic properties of all the compounds within the scope of formula (I).

TABLE I

Structure: Ar—C(=O)—NH—CH₂—CH₂—N (spiro piperidine with N-phenyl-R¹ and carboxamide NH group)

| Ar | R¹ | Base or Salt form | ED₅₀ in mg/kg s. c. |
|---|---|---|---|
| phenyl | H | base | 0.10 |
| 4-F-phenyl | H | HCl | 0.06 |
| 2-Cl-phenyl | H | HCl | 0.06 |
| 2-Br-phenyl | H | HCl | 0.25 |
| 4-OCH₃-phenyl | H | base | 0.50 |
| 3-CH₃-phenyl | H | HCl | 0.10 |
| 3-H₂N-4-F-phenyl | H | HCl·H₂O | 0.004 |
| 4-F-phenyl | 4-F | HCl | 0.015 |
| 3-Cl-4-F-phenyl | 4-F | HCl | 0.002 |
| 4-F-phenyl | 4-F | HCl | 0.03 |
| 3-O₂N-4-F-phenyl | 4-F | HCl | 0.20 |
| 4-HO-phenyl | 4-F | HCl | 0.20 |

TABLE I-continued

| Ar | R¹ | Base or Salt form | ED₅₀ in mg/kg s. c. |
|---|---|---|---|
| 2-O₂N-phenyl | 4-F | HCl | 0.12 |
| thiophene | H | base | 0.45 |
| 2-Cl-phenyl | 4-F | HCl | 0.004 |
| 3-Cl-phenyl | H | HCl | 0.63 |
| 3-F-phenyl | H | HCl | 0.25 |
| 4-Cl-phenyl | H | base | 0.80 |
| 4-NO₂-phenyl | H | base | ≥0.63 |
| 3-Cl-4-O₂N-phenyl (substituted) | H | base | 0.25 |
| 3-H₂N-4-F-phenyl | 4-F | HCl·H₂O | 0.002 |
| 3-Cl-4-F-phenyl | H | HCl | 0.015 |
| furan | 4-F | HCl | ≥0.63 |

TABLE I-continued

Ar—C(=O)—NH—CH₂—CH₂—N(piperidine with N-phenyl-R¹ and C(=O)NH-ethyl substituents)

| Ar | R¹ | Base or Salt form | ED$_{50}$ in mg/kg s. c. |
|---|---|---|---|
| 2-H₂N-phenyl | 4-F | base | 0.008 |
| 1-methylpyrrol-2-yl | 4-F | HCl | 0.25 |
| 2-(NH-CO-CH₃)-5-F-phenyl | 4-F | base | 0.07 |

TABLE II

Ar—C(=O)—NH—CH₂—CH₂—N(piperidine spiro-fused to benzimidazolin-2-one with R³ substituent)

| Ar | R³ | Base or Salt form | ED$_{50}$ in mg/kg s.c. |
|---|---|---|---|
| phenyl | H | base | 0.20 |
| 2-F-phenyl | H | base | 0.50 |
| 4-F-phenyl | H | base | 0.12 |
| 3-CH₃-phenyl | H | base | 0.25 |
| 2-CH₃-phenyl | H | base | 0.50 |
| 2-O₂N-4-F-phenyl | H | base | 0.50 |
| 4-F-phenyl | 5-Cl | base | 0.08 |
| 2-Cl-4-F-phenyl | 5-Cl | base | 0.03 |
| 2-H₂N-4-F-phenyl | H | base | 0.03 |
| 2-Cl-phenyl | H | base | 1.5 |
| 2-H₂N-phenyl | 5-Cl | base | 0.45 |
| 2-H₂N-phenyl | H | base ½H₂O | 0.10 |
| 2-(NH-CO-CH₃)-4-F-phenyl | H | base | 0.04 |
| 2-(NH-CO-CH₃)-4-F-phenyl | 5-Cl | base | 0.06 |
| 2-O₂N-4-F-phenyl | 5-Cl | HCl | 0.25 |

TABLE III

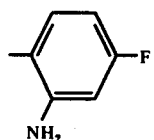

| Ar | R[6] | Base or Salt form | ED$_{50}$ in mg/kg S.C. |
|---|---|---|---|
| (4-F, 3-NH$_2$ phenyl) | 4-Cl | 2 . HCl | 0.70 |

TABLE IV

Ar—C(=O)—NH—CH$_2$—CH$_2$—N⟨A⟩

| Compound | Base or Salt form | ED$_{50}$ in mg/kg s.c. |
|---|---|---|
| (F-phenyl-C(=O)-NH-CH$_2$-CH$_2$-N-piperidine with benzimidazolone N-CH$_2$-CH$_2$CN) | base | 0.50 |
| (F-phenyl-C(=O)-NH-CH$_2$-CH$_2$-N-piperidine with benzimidazole N=CO-CH$_3$) | base | 0.63 |
| (F-phenyl-C(=O)-NH-CH$_2$-CH$_2$-N-tetrahydropyridine with N-C(=O)NH-o-tolyl) | base | 0.25 |

The compounds of formula (I) are potent psychotropic agents and as such they can be used in the treatment of metal disorders such as, for example, personality and psycho-affective disorders and schizophrenia. The psychotropic activity of the subject compounds (I) is strongly evidenced by the experimental data obtained in the apomorphine test in rats, a test which is indicative for central nervous system depressant activity. The test was carried out following the procedure described hereafter and the experimental data which were obtained are summarized in Table V wherein the compound numbers refer to the corresponding structures in the Tables I to IV.

The compounds listed in table V are not given for the purpose of limiting the invention thereto but only in order to exemplify the useful psychotropic properties of all the compounds within the scope of formula (I).

The apomorphine test in rats

The experimental animals used in this test were adult male Wistar rats (weight 240 ± 10 g.). After an overnight fast, the animals were treated subcutaneously (1ml/100 g) with an aqueous solution of the compound under investigation and put into isolated observation cages. Thirty minutes thereafter, 1.25 mg/kg of apomorphine hydrochloride was injected intravenously and the rats were observed over a 1 hour period for the presence or absence of the following apomorphine-induced phenomena: agitation and stereotypic chewing. Table V gives the lowest effective dose (LED), i.e., the dose level, the effect of which statistically significantly different from that observed in the corresponding untreated controls (Fisher exact probability test).

TABLE V:

Anti-apomorphine activity of the compounds (I) in rats.

| Compound no. | LED in mg/kg s.c. |
|---|---|
| 2 | 5 |
| 3 | 0.31 |
| 4 | 2.5 |
| 6 | 2.5 |
| 7 | 2.5 |
| 8 | 10 |
| 9 | 0.63 |
| 11 | 10 |
| 14 | 0.63 |
| 16 | 1.25 |
| 20 | 5 |
| 21 | 2.5 |
| 23 | 2.5 |
| 24 | 10 |
| 25 | 5 |
| 27 | 5 |
| 31 | .5 |
| 32 | 1.25 |
| 33 | 5 |
| 34 | 5 |
| 36 | ≥10 |
| 37 | 10 |
| 38 | 10 |

TABLE V:-continued

| Anti-apomorphine activity of the compounds (I) in rats. | |
|---|---|
| Compound no. | LED in mg/kg s.c. |
| 40 | 5 |

In view of their useful antiemetic and psychotropic activity, the subject compounds may be formulated into various pharmaceutical forms for administration purposes. To prepare the pharmaceutical compositions of this invention, an effective antiemetic or psychotropic amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example may be prepared in which the carrier comprises saline solution, glucose solution or a mixture of saline and glucose solution. Injectable suspensions may also be prepared in which case appropriate liquid carriers, suspending agents and the like may be employed. Acid additions salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The amount of active ingredient per dosage unit for either antiemetic or psychotropic purposes will be from about 1 to about 200 mg and, preferably from about 5 to about 100 mg.

The following formulations exemplify typical antiemetic and psychotropic pharmaceutical compositions in dosage unit form suitable for systemic administration to animal and human subjects in accordance with the instant invention.

Oral drop

The following formulation provides 10 liters of an oral-drop solution comprising 5 milligrams of N-{2-[4-chloro-2,3-dihydro-2-oxo-1H-benzimidazol-1-yl)-1-piperidinyl]ethyl}-4-fluorobenzamide as the active ingredient per ml.

| A.I. | 50 | grams |
|---|---|---|
| 2-Hydroxypropanoic acid | 2.5 | milliliters |
| Methyl 4-hydroxybenzoate | 18 | grams |
| Propyl 4-hydroxybenzoate | 2 | grams |
| Pyrogen-free water q.s. ad 10 liters | | |

The methyl and propyl 4-hydroxybenzoates are dissolved in about 5 liters of boiling pyrogen-free water. After cooling to about 50° C there are added while stirring the 2-hydroxypropanoic acid and thereafter the A.I.. The solution is cooled to room temperature and supplemented with pyrogen-free water ad volume. The solution is sterilized by filtration (U.S.P. XVII p. 811) and filled in sterile containers.

Injectable solution

The oral drop solution described herebefore may be used as an injectable solution.

Capsules 10,000 Hard gelatine capsules, each containing as the active ingredient (A.I.) 20 milligrams of N-{2-[4-(5-chloro-2,3-dihydro-2-oxo-1H-benzimidazol-1-yl)-1-piperidinyl]ethyl}-4-fluoro benzamide, are prepared from the following composition.

| | Grams |
|---|---|
| A.I. | 200 |
| Lactose | 1000 |
| Starch | 300 |
| Talc | 300 |
| Calcium stearate | 10 |

An uniform mixture of the active and supplementary ingredients is prepared and filled into two-piece hard gelatine capsules.

Tablets

5000 Compressed tablets, each containing as the active ingredient (A.I.) 25 milligrams of N-{2-[4-(5-chloro-2,3-dihydro-2-oxo-1H-benzimidazol-1yl)-1-piperidinyl]ethyl}-4-fluorobenzamide, are prepared from the following formulation.

| | Grams |
|---|---|
| A.I. | 125 |
| Starch | 150 |
| Dibasic calcium phosphate hydrous | 650 |
| Calcium stearate | 35 |

The finely powdered ingredients are mixed well and granulated with 10% starch paste. The granulation is dried and compressed into tablets.

Oral suspension

The following formulation provides 5 liters of an oral suspension comprising as an active ingredient (A.I.) 15 milligrams of N-{2-[4-(5-chloro-2,3-dihydro-2-oxo-1H- benzimidazol-1-yl)-1-piperidinyl] ethyl}-4-fluorobenzamide per teaspoonfull (5 milliliters).

| | Grams |
|---|---|
| A.I. | 15.0 |
| Sucrose | 300.0 |
| Dioctyl sodium sulfosuccinate | 0.5 |
| Bentonite | 22.5 |
| Methyl paraben | 7.5 |
| Propyl paraben | 1.5 |
| Antifoam A.F. Emulsion | 0.15 |
| Propylene Glycol | 52.0 |
| FD & C Yellow No. 5 | 0.1 |
| Sodium cyclamate | 50.0 |
| Sodium saccharin | 5.0 |
| Orange Flavor | 7.5 |
| Filtered purified water, q.s., ad | 5 liters |

Dissolve the parabens in the propylen glycol and add this solution to a solution of the sodium cyclamate, sodium saccharin and sucrose in half the water. Suspend the bentonite in hot (about 85° C) water and stir for 60 minutes. Add the bentonite solution to the former solution. Dissolve the sulfosuccinate in some water and suspend the A.I. in the resulting solution. Add the Antifoam A.F. Emulsion which has beed diluted to a lotion consistency with a minimum amount of water and mix well. Add the latter suspension of A.I. to the former mixture and mix well. Add the FD&C Yellow No. 5 dissolved in a small amount of water. Add the orange flavor, q.s. to volume with water, and stir to a homogeneous mixture. Pass the mixture through a colloid mill and fill into suitable containers.

In view of the antiemetic activity of the subject compounds, it is evident that the present invention provides a method of inhibiting emesis in warm-blooded animals affected by emesis by the systemic administration of an effective antiemetic amount of a compound of formula (I) and the pharmaceutically acceptable acid addition salts thereof in admixture with a pharmaceutical carrier.

In addition, in view of the psychotropic activity of the subject compounds, the present invention also provides a method of treating mental disorders in warm-blooded animals affected by such disorders, by the systemic administration of an effective psychotropic inhibiting amount of a compound of formula (I) and the pharmaceutically acceptable acid addition salts thereof in admixture with a pharmaceutical carrier.

The following examples are intended to illustrate but not to limit the scope of the present invention. Unless otherwise stated all parts therein are by weight.

EXAMPLE I

To 231 parts of a aziridine solution 0.95M in water are added 16 parts of sodium hydrogen carbonate while stirring vigorously at 0° C. Then there is added dropwise, during a 45 minutes-period, a solution of 36 parts of 4-fluoro-2-methoxybenzoyl chloride in 150 parts of trichloromethane while still cooling at 0° C. Upon completion, stirring is continued for 30-45 minutes without cooling. The reaction mixture is adjusted to pH 8 with a diluted sodium hydroxide solution and the product is extracted three times with trichloromethane. The combined extracts are washed three times with water, dried, filtered and evaporated, yielding 40.5 parts of 1-(4-fluoro-2-methoxybenzoyl)-aziridine as a residue.

EXAMPLE II

To 690 parts of a solution of aziridine in water 0.875M are added 42 parts of sodium hydrogen carbonate while cooling in an ice-salt bath at −5° C. While stirring vigorously, there is added dropwise, during a 30 minutes period, a solution of 78.8 parts of 2-hydroxybenzoyl chloride in 150 parts of trichloromethane at a temperature below 5° C. The reaction mixture is allowed to reach 25° C while stirring, and a diluted sodium hydroxide solution is added to pH 8. The product is extracted three times with trichloromethane. The combined extracts are washed three times with water, dried, filtered and evaporated, yielding 56 parts of 1-(2-hydroxybenzoyl)aziridine as a residue.

EXAMPLE III

To a stirred mixture of 76 parts of 4-fluoro-2-nitrobenzoic acid and 225 parts of benzene are added dropwise 71 parts of sulfinyl chloride. Upon completion, stirring is continued first for 5 hours at reflux and further overnight at room temperatue. The reaction mixture is evaporated. The residue is taken up twice in benzene and the latter is evaporated each time, yielding 85 parts of 4-fluoro-2-nitrobenzoyl chloride as a residue.

To a mixture of 21.6 parts of aziridine and 37.8 parts of sodium hydrogen carbonate is added dropwise a solution of 85 parts of 4-fluoro-2-nitro benzoyl chloride in 75 parts of trichloromethane while stirring vigorously at 0° C. Upon completion, stirring vigorously is continued for 30 minutes without cooling. After warming to 25° C, the reaction mixture is adjusted to pH 8 with a diluted sodium hydroxide solution. The product is extracted three times with trichloromethane. The combined extracts are washed with water, dried filtered and evaporated, yielding 75 parts of 1-(4-fluoro-2-nitrobenzoyl)aziridine as a residue.

EXAMPLE IV

To a cooled (0° c) mixture of 338 parts of a solution of aziridine in water 0.875 N and 22 parts of sodium hydrogen carbonate are added dropwise, during a 45 minutes-period, 87 parts of 2-thiophenecarbonyl chloride while stirring vigorously. Upon completion, stirring is continued for 45 minutes without cooling. The reaction mixture is warmed to room temperature and alkalized with a diluted sodium hydroxide solution till pH 8 is reached. The product is extracted three times with trichloromethane. The combined extracts are washed with water, dried, filtered and evaporated, yielding 42 parts of 1-(2-thienylcarbonyl)aziridine as a residue.

EXAMPLE V

A mixture of 12.94 parts of ethyl (2-bromoethyl)carbamate, 13.51 parts of 1,3-dihydro-1-(4-piperidinyl)-2H-benzimidazol-2-one, 10.1 parts of sodium hydrogen carbonate and 160 parts of ethanol is stirred and refluxed overnight. The reaction mixture is cooled, filtered over hyflo and the filtrate is evaporated. The residue is purified by column-chromatography over silica gel using a mixture of trichloromethane, 10% of methanol and one drop of ammonium hydroxide, as eluent. The pure fractions are collected and the eluent is evaporated, yielding 4.4 parts of ethyl 2-[4-(2,3-dihydro-2-oxo-1H-benzimidazol-1-yl)-1-piperidinyl]ethylcarbamate as a residue.

A mixture of 0.333 parts of ethyl 2-[4-(2,3-dihydro-2-oxo-1H-benzimidazol-1-yl)-1-piperidinyl]ethylcarbamate, 1.65 parts of hydrobromic acid solution 48% and 0.11 parts of water is stirred and refluxed for 2 hours. The hydrobromic acid and water are evaporated. The residue is taken up three times in benzene, while each time the latter is evaporated. The oily residue is crystallized from 2- propanol. The product is filtered off and recrystallized from a small amount of ethanol, yielding 0.27 parts of 1-[1-(2-aminoethyl)-4-piperidinyl]-1,3-dihydro-2H-benzimidazol-2-one dihydrobromide; mp. +300° C(dec).

EXAMPLE VI

A mixture of 0.74 parts of 1-(benzoyl)aziridine, 1.16 parts of 1-phenyl-1,3,8-triazaspiro[4,5]decan-4-one, 7.2 parts of benzene and 0.8 parts of methanol is stirred and refluxed for 2 hours. The reaction mixture is cooled, 1,1'-oxybisethane is added and the whole is boiled in ethyl acetate. After cooling, the precipitated product is filtered off and crystallized from ethanol 70%, yielding, after drying in vacuo at 80° C. 0.67 parts of N-[2-(4-oxo-1-phenyl-1,3,8-triazaspiro[4,5]dec-8-yl)ethyl]-benzamide; mp. 198.4° C.

EXAMPLE VII

A mixture of 1.82 parts of 1-(4-chlorobenzoyl)aziridine, 2.32 parts of 1-phenyl-1,3,8-triazaspiro[4,5]decan-4-one, 10.8 parts of benzene an 1.6 parts of methanol is stirred and refluxed for 1.50 hours. The reaction mixture is cooled and upon scratching, the product solidifies. It is filtered off, washed with benzene and crystallized from 2-propanol, yielding 1.53 parts of 4-chloro-N-[2-(4-oxo-1-phenyl-1,3,8-triazaspiro[4,5]-dec-8-yl)ethyl]benzamide; mp. 200.6° C.

EXAMPLE VIII

Following the procedure of Example VII and using equivalent amounts of the appropriate starting materials, the following compounds are prepared:
4-nitro-n-2-(4-oxo-1-phenyl-1,3,8-triazasphiro[4,5]-dec-8-yl)- ethyl]-benzamide; mp. 225.7° C.
4-methoxy-N-[2-(4-oxo-1-phenyl-1,3,8-triazaspiro[4,5]dec-8-yl)-ethyl]benzamide; mp. 200.9° C;
2,4-dichloro-N-[2-(4-oxo-1-phenyl-1,3,8-triazaspiro[4,5]dec-8-yl)ethyl]benzamide; mp. 205.7° C;
2-ethoxy-N-{2-[4-oxo-1-phenyl-1,3,8-triazaspiro[4,5]-dec-8-yl]ethyl}benzamide; mp. 205.8° C;
2-methoxy- N-[2-(4-oxo-1-phenyl-1,3,8-triazaspiro[4,5]dec-8-yl)-ethyl]benzamide; mp. 195° C;
2-methoxy-4-nitro-N-[2-(4-oxo-1-phenyl-1,3,8-triazaspiro[4,5]-dec-8-yl)ethyl]benzamide; mp. 205.8° C; and
2-chloro-4-nitro-N-[2-(4-oxo-1-phenyl-1,3,8-triazaspiro[4,5]dec-8-yl)ethyl]benzamide; mp. 190° C.

EXAMPLE IX

A mixture of 7.7 parts of 1-(2-thienylcarbonyl)aziridine, 11.5 parts of 1-phenyl-1,3,8-triazaspiro[4,5]decan-4-one, 8 parts of methanol and 54 parts of benzene is stirred and refluxed for 1.50 hours. The reaction mixture is cooled and dissolved in trichloromethane. The solution is washed twice with water, dried, filtered and evaporated. The residue is crystallized from methanol. The product is filtered off and dried, yielding 2 parts of N-[2-(4-oxo-1-phenyl-1,3,8-triazaspiro[4,5]-dec-8-yl)ethyl]-2-thiophenecarboxamide; mp. 194° C.

EXAMPLE X

A mixture of 15 parts of 1-(4-fluoro-2-nitrobenzoyl)-aziridine, 12 parts of 1-phenyl-1,3,8-triazaspiro[4,5]decan-4-one, 8.8 parts of methanol and 56 parts of benzene is stirred first for 1.50 hours at reflux and further overnight at room temperature. The reaction mixture is evaporated. The residue is dissolved in trichloromethane and the solution is washed with water. Then there are added 8 parts of methanol and silica gel and the whole is stirred for 10 minutes. The silica gel is filtered off and the filtrate is evaporated. The residue is stirred in 2,2'-oxybispropane. The product is filtered off and crystallized from 4-methyl-2-pentanone. It is filtered off and dried, yielding 13 parts of 4-fluoro-2-nitro-N-[2-(4-oxo-1-phenyl-1,3,8-triazaspiro-[4,5]dec-8-yl)ethyl]benzamide; mp. 160° C.

EXAMPLE XI

A mixture of 1.68 parts of 1-(4-fluorobenzoyl)aziridine, 2.5 parts of 1-(4-fluorophenyl)-1,3,8-triazaspiro[4,5]-decan-4-one, 10.8 parts of benzene and 1.6 parts of methanol is stirred and refluxed for 1.50 hours. The reaction mixture is cooled and acidified with 2-propanol, previously saturated with gaseous hydrogen chloride. The formed hydrochloride salt is filtered off and crystallized from a mixture of ethanol and water (8:2 by volume), yieldng, after drying, 2.4 parts of 4-fluoro-N-{2-[1-(4-fluorophenyl)-4-oxo-1,3,8-triazaspiro[4,5]dec-8-yl]ethyl}-benzamide hydrochloride; mp. 279.6° C.

EXAMPLE XII

In the same manner as described in Example XI and using equivalent amounts of the appropriate starting materials, the following compounds are prepared:
N-[2-(4-oxo-1-phenyl-1,3,8-triazaspiro[4,5]dec-8-yl)ethyl]-benzamide hydrochloride; mp. 259.4° C;
4-fluoro-N-[2-(4-oxo-1-phenyl-1,3,8-triazaspiro[4,5]-dec-8-yl)ethyl]benzamide hydrochloride; mp. 266.4° C;
2-chloro-N-[2-(4-oxo-1-phenyl-1,3,8-triazaspiro[4,5]-dec-8-yl)ethyl]benzamide hydrochloride; mp. 256.6° C; and
N-{2-[1-(4-fluorophenyl)-4-oxo-1,3,8-triazaspiro[4,5]dec-8-yl]ethyl}-4-methylbenzamide hydrochloride; mp. 261.2° C.

EXAMPLE XIII

A mixture of 1.68 parts of 1-(2-fluorobenzoyl)-aziridine, 2.32 parts of 1-phenyl-1,3,8-triazaspiro[4,5]decan-4-one, 10.8 parts of benzene and 1.6 parts of methanol is stirred and refluxed for 1.50 hours. The reaction mixture is diluted with 2-propanone and 2-propanol, saturated with gaseous hydrogen chloride, is added. The formed hydrochloride salt is filtered off and crystallized from ethanol, yielding, after drying 1.98 parts of 2-fluoro-N-[2-(4-oxo-1-phenyl-1,3,8-triazaspiro[4,5]dec-8-yl)ethyl]benzamide hydrochloride; mp. 242.8° C.

EXAMPLE XIV

Following the procedure of Example XIII and using equivalent amounts of the appropriate starting materials, the following compounds are obtained:
2-chloro-4-fluoro-N-[2-(4-oxo-1-phenyl-1,3,8-triazaspiro[4,5]-dec-8-yl)ethyl]benzamide hydrochloride; mp. 263.8° C;
2-chloro-4-fluoro-N-{2-[1-(4-fluorophenyl)-4-oxo-1,3,8-triazaspiro[4,5]dec-8-yl]ethyl}benzamide hydrochloride; mp. 269.8° C;
2-chloro-N-{2-[1-(4-fluorophenyl)-4-oxo-1,3,8-triazaspiro[4,5]-dec-8-yl]ethyl}benzamide hydrochloride; mp. 252.6° C;

2-bromo-N-[2-(4-oxo-1-phenyl-1,3,8-triazaspiro[4,5]-dec-8-yl)ethyl]benzamide hydrochloride; mp. 260.6° C; and
2-methyl-N-[2-(4-oxo-1-phenyl-1,3,8-triazaspiro[4,5]-dec-8-yl)ethyl]benzamide hydrochloride; mp. 251.9° C.

EXAMPLE XV

A mixture of 7.6 parts of 1-(2-nitrobenzoyl)aziridine, 9.97 parts of 1-(4-fluorophenyl)-1,3,8-triazaspiro[4,5]decan-4-one, 43.2 parts of benzene and 6.4 parts of methanol is stirred and refluxed for 1.50 hours. Trichloromethane is added and the whole is washed three times with water. The undissolved precipitate is filtered off and the organic phase is dried, filtered and evaporated. The residue is converted into the hydrochloride salt in 2-propanone and 2-propanol. The salt is filtered off and crystallized from a mixture of ethanol and water. It is filtered off and dried in vacuo, yielding 2.7 parts of N-{2-[1-(4-fluorophenyl)-4-oxo1,3,8-triazaspiro[4,5]dec-8-yl]ethyl}-2-nitrobenzamide hydrochloride; m.p. 267.2° C.

EXAMPLE XVI

A mixture of 6.5 parts of 1-(2-hydroxybenzoyl)aziridine, 5 parts of 1-(4-fluorophenyl-1,3,8-triazaspiro 4,5]decan-4-one, 43.2 parts of benzene an 6.4 parts of methanol is stirred and refluxed for 1.50 hours. The reaction mixture is taken up in trichloromethane. The resulting solution is washed three times with water, dried, filtered and evaporated. The residue is converted into the hydrochloride salt in ethanol and 2-propanol. The salt is filtered off and crystallized from methanol, yielding 2.6 parts of N-{2-[1-(4-fluorophenyl)-4-oxo-1,3,8-triazaspiro[4,5]dec-8-yl]ethyl}-2-hydroxybenzamide hydrochloride; mp. 279.4° C.

EXAMPLE XVII

A mixture of 4.6 parts of 1-(4-methylbenzoyl)-aziridine, 4.6 parts of 1-phenyl-1,3,8-triazaspiro[4,5]decan-4-one, 21.6 parts of benzene and 3.2 parts of methanol is stirred and refluxed for 1.50 hours. After cooling to room temperature, the precipitated product is filtered off and converted into the ethanedioate salt in 4-methyl-2-pentanone. The salt is filtered off and crystallized from a mixture of methanol and water (10:1 by volume), yielding 3.5 parts of 4-methyl-N-[2-(4-oxo-1-phenyl-1,3,8-triazaspiro[4,5]dec-8-yl)ethyl]benzamide ethanedioate; mp. 229.8° C.

EXAMPLE XVIII

A mixture of 11 parts of 1-(4-fluoro-2-nitrobenzoyl)aziridine, 13 parts of 1-(4-fluorophenyl)-1,3,8-triazaspiro[4,5]decan -4-one, 55.8 parts of benzene and 8.8 parts of methanol is stirred first for 1.50 hours at reflux temperature and further overnight at room temperature. The reaction mixture is evaporated and the residue is taken up in trichloromethane. The solution is washed with water and stirred for 10 minutes with 6.4 parts of methanol and silica gel. The latter is filtered off and the filtrate is evaporated. The residue is triturated in 2,2'-oxybispropane. The product is filtered off and converted into the hydrochloride salt in 2-propanone and 2-propanol. The salt is filtered off and crystallized from a mixture of methanol and water, yielding, after drying, 12 parts of 4-fluoro-N-{2-[1-(4-fluorophenyl)-4-oxo-1,3,8-triazaspiro[4,5]dec-8-yl]ethyl}-2-nitrobenzamide hydrochloride; mp. 271.3° C.

EXAMPLE XIX

A mixture of 1.2 parts of N-(2-bromoethyl)-2-nitrobenzamide, 1.15 parts of 1-phenyl-1,3,8-triazaspiro[4,5]decan-4-one and 45 parts of N,N-dimethylformamide is stirred and refluxed for 3 hours. After stirring is continued overnight at room temperature, N,N-dimethylformamide is evaporated in vacuo at 80° C. The residue is boiled in a mixture of 2-propanone and water and the unreacted starting material is filtered off. The filtrate is concentrated to half its volume and 2-propanol is added to the concentrate. The precipitated product is filtered off and dried, yielding 7 parts of 2-nitro-N-[2-(4-oxo-1-phenyl-1,3,8-triazaspiro[4,5]-dec-8-yl)-ethyl]benzamide hydrobromide; mp. 259.4° C.

EXAMPLE XX

A mixture of 8 parts of 4-fluoro-2-nitro-N-[2-(4-oxo-1-phenyl-1,3,8-triazaspiro[4,5]dec-8-yl)ethyl]benzamide, 40 parts of methanol and 90 parts of tetrahydrofuran is hydrogenated at normal pressure and at room temperature with 3 parts of Raney-nickel catalyst. After the calculated amount of hydrogen is taken up, the catalyst is filtered off and the filtrate is evaporated. The residue is converted into the hydrochloride salt in 2-propanol. The salt is filtered off and crystallized from ethanol, yielding 1 part of 2-amino-4-fluoro-N-[2-(4-oxo-1-phenyl-1,3,8-triazaspiro[4,5]dec-8-yl)ethyl]-benzamide hydrochloride hydrate; mp. 167.3° C.

EXAMPLE XXI

A mixture of 8 parts of 4-fluoro-N-{2-[1-(4-fluorophenyl)-4-oxo-1,3,8-triazaspiro[4,5]dec-8-yl]ethyl}-2-nitrobenzamide hydrochloride, 120 parts of methanol and 25 parts of water is hydrogenated at normal pressure and at room temperature with 5 parts of Raney-nickel catalyst. After the calculated amount of hydrogen is taken up, the catalyst is filtered off and the filtrate is evaporated. The residue is crystallized from methanol. The product is filtered off and recrystallized from ethanol, yielding 1 part of 2-amino-4-fluoro-N-{2-[1-(4-fluorophenyl)-4-oxo-1,3,8-triazaspiro[4,5]dec-8-yl]ethyl}benzamide hydrochloride hydrate; mp. 223.5° C.

EXAMPLE XXII

A mixture of 0.74 parts of 1-(benzoyl)aziridine, 1.09 parts of 1,3-dihydro-1-(4-piperidinyl)-2H-benzimidazol-2-one, 7.2 parts of benzene and 0.8 parts of methanol is stirred and refluxed for 2 hours. The reaction mixture is cooled and upon the addition of 1,1'-oxybisethane, the product is precipitated. The latter is filtered off and crystallized from 2-propanol, yieldjg 1.24 parts of N-{2-[4-(2,3-dihydro-2-oxo-1H-benzimidazol-1-yl)-1-piperidinyl]-ethyl}benzamide; mp. 223.9° C.

EXAMPLE XXIII

In a similar manner as described in Example XXII, the following compounds are prepared by the reaction of an appropriate aroylaziridine with an appropriate piperidine derivative;
2-ethoxy-N-{2-[4-(2,3-dihydro-2-oxo-1H-benzimidazol-1-yl)-1-piperidinyl]ethyl}benzamide; mp. 192.8° C;

N-{2-[4-(2,3-dihydro-2-oxo-1H-benzimidazol-1-yl)-1-piperidinyl]-ethyl}-4-fluorobenzamide; mp. 231° C; and
2-bromo-N-{2-[4-(2,3-dihydro-2-oxo-1H-benzimidazol-1-yl)-1-piperidinyl]ethyl}benzamide; mp. 204.4° C.

EXAMPLE XXIV

A mixture of 1.68 parts of 1-(4-fluorobenzoyl)-aziridine, 2.53 parts of 5-chloro-1,3-dihydro-1-(4-piperidinyl)-2H-benzimidazol-2-one, 10.8 parts of benzene and 1.6 parts of methanol is stirred and refluxed for 1.50 hours. The precipitated product is sucked off and washed with 2-propanone. The product is crystallized from 2-propanol, yielding, after drying, 2.47 parts of N-{2-[4-(5-chloro-2,3-dihydro-2-oxo-1H-benzimidazol-1-yl)-1-piperidinyl] ethyl}-4-fluorobenzamide; mp. 239.6° C.

EXAMPLE XXV

Following the procedures of Example XXIV and using equivalent amounts of the appropriate starting materials, the following compounds are obtained:
N-{2-[4-(2,3-dihydro-2-oxo-1H-benzimidazol-1-yl)-1-piperidinyl] ethyl}-2-fluorobenzamide; mp. 197.3° C;
4-chloro-N-{2-[4-(2,3-dihydro-2-oxo-1H-benzimidazol-1-yl)-1-piperidinyl] ethyl}benzamide; mp. 236.9° C;
2-chloro-N-{2-[4-(2,3-dihydro-2-oxo-1H-benzimidazol-1-yl)-1-piperidinyl] ethyl}benzamide; mp. 196.4° C;
N-{2-[4-(2,3-dihydro-2-oxo-1H-benzimidazol-1-yl)-1-piperidinyl]-ethyl} -4-methoxybenzamide; mp. 259.2° C;
N-{2-[4-(2,3-dihydro-2-oxo-1H-benzimidazol-1-yl)-1-piperidinyl]-ethyl} -2-methylbenzamide; mp. 217.2° C;
2-chloro-N-{2-[4-(5-chloro-2,3-dihydro-2-oxo-1H-benzimidazol-1-yl)-1-piperidinyl] ethyl}-4-fluorobenzamide; mp. 225° C;
N-{2-[4-(2,3-dihydro-2-oxo-1H-benzimidazol-1-yl)-1-piperidinyl]-ethyl} -2-methoxy-4-nitrobenzamide; mp. 248.8° C;
2-chloro-N-{2-[4-(2,3-dihydro-2-oxo-1H-benzimidazol-1-yl)-1-piperidinyl] ethyl}-4-nitrobenzamide hydrate; mp. 208.8°–209.9° C;
4-fluoro-N-{2-[4-(2,3-dihydro-2-oxo-1H-benzimidazol-1-yl)-1-piperidinyl] ethyl}-2-nitrobenzamide; mp. 196.8° C;
N-{2-[4-(2,3-dihydro-2-oxo-1H-benzimidazol-1-yl)-1-piperidinyl] ethyl}-2-hydroxybenzamide hydrochloride hemi-2-propanolate; mp. 206.2° C; and
N-{2-[4-(5-chloro-2,3-dihydro-2-oxo-1H-benzimidazol-1-yl)-1-piperidinyl] ethyl}-2-hydroxybenzamide hydrochloride hemihydrate; mp. 296.6° C.

EXAMPLE XXVI

A mixture of 8 parts of 1-(4-fluor-2-methoxybenzoyl)-aziridine, 3.8 parts of 1,3-dihydro-1-(4-piperidinyl)-2H-benzimidazol-2-one, 54 parts of benzene and 8 parts of methanol is stirred and refluxed for 1.50 hours. The reaction mixture is cooled and 90 parts of benzene are added. The whole is washed with water and the layers are separated. The organic phase is dried, filtered and evaporated. The residue is crystallized from 2-propanone. The product is filtered off and dried, yielding 4 parts of N-{2-[4-(2,3-dihydro-2-oxo-1H-benzimidazol-1-yl)-1-piperidinyl] ethyl}-4-fluoro-2-methoxybenzamide; mp. 197.3° C.

EXAMPLE XXVII

A mixture of 8 parts of 1-(4-fluoro-2-methoxybenzolyl)-aziridine, 4.4 parts of 5-chloro-1,3-dihydro-1-(4-piperidinyl)-2H-benzimidazol-2-one, 135 parts of benzene and 8 parts of methanol is stirred and refluxed for 1.50 hours. The reaction mixture is cooled and the formed precipitate is filtered off. The filtrate is washed with water, whereupon a solid product precipitates, which dissolves again by the addition of trichloromethane. The layers are separated. The organic phase is dried, filtered and evaporated. The residue is crystallized from 2-propanone. The product is filtered off and recrystallized from a mixture of 2-propanone and water, yielding 2.2 parts of N-{2-[4-(5-chloro-2,3-dihydro-2-oxo-1H-benzimidazol-1-yl)-1-piperidinyl]-ethyl}-4-fluoro-2-methoxybenzamide; mp. 227.3° C.

EXAMPLE XXVIII

A mixture of 7.7 parts of 1-(2-thienylcarbonyl)aziridine, 10.8 parts of 1,3-dihydro-1-(4-piperidinyl)-2H-benzimidazol-2-one, 54 parts of benzene and 8 parts of methanol is stirred and refluxed for 1.50 hours. The reaction mixture is cooled and trichloromethane is added. The undissolved product is filtered off and stirred in 2,2'-oxybispropane. It is filtered off again and crystallized twice: first from a mixture of methanol and N,N-dimethylformamide and then from a mixture of trichloromethane and methanol, yielding 4 parts of N-{2-[4-(2,3-dihydro-2-oxo-1H-benzimidazol-1-yl)-1-piperidinyl] ethyl}-2-thiophenecarboxamide; mp. + 300° C (dec.).

EXAMPLE XXIX

A mixture of 7.6 parts of 1-(2-nitrobenzoyl)aziridine, 8.6 parts of 1,3-dihydro-1-(4-piperidinyl)-2H-benzimidazol-2-one, 6.4 parts of methanol and 43.2 parts of benzene is stirred and refluxed for 1.50 hours. The reaction mixture is evaporated. The residue is purified by column-chromatography over silica gel using a mixture of trichloromethane and 10% of methanol as eluent. The pure fractions are collected and the eluent is evaporated. The residue is converted into the hydrochloride salt in 2-propanol. The salt is filtered off and crystallized from ethanol, yielding 2.5 parts of N-{2-[4-(2,3-dihydro-2-oxo-1-benzimidazol-1-yl)-1-piperidinyl] ethyl}-2-nitrobenzamide hydrochloride; mp. 263.6°–265° C.

EXAMPLE XXX

A mixture of 2.3 parts of 1-(4-methyl-benzoyl)aziridine, 2.5 parts of 5-chloro-1,3-dihydro-1-(4-piperidinyl)-2H-benzimidazol-2-one, 10.8 parts of benzene and 1.6 parts of methanol is stirred and refluxed for 1.50 hours. The reaction mixture is allowed to cool to room temperature. The precipitated product is filtered off and converted into the ethanedioate salt in 4-methyl-2-pentanone. The salt is filtered off and crystallized twice first from a mixture of methanol and 2,2'-oxybispropane (1:1 by volume) and then from ethanol, yielding 2 parts of N-{2-[4-(5-chloro-2,3-dihydro-2-oxo-1H-benzimidazol-1-yl)-1-piperidinyl} ethyl}-4-methylbenzamide ethanedioate; mp. 230.9° C.

EXAMPLE XXXI

A mixture of 4.6 parts of 1-(4-methylbenzoyl)-aziridine, 4.34 parts of 1,3-dihydro-1-(4-piperidinyl)-2H-benzimidazol-2-one, 21.6 parts of benzene and 3.2 parts of methanol is stirred and refluxed for 1.50 hours. After cooling to 0° C, the precipitated product is filtered off and converted into the ethanedioate salt in 4-methyl-2-pentanone. The salt is filtered off and crystallized from methanol, yielding 2.2 parts of N-{2-[4-(2,3dihydro-2-oxo-1H-benzimidazol-1-yl)1-piperidinyl]-ethyl}-4-methylbenzamide ethanedioate; mp. 227.6° C.

EXAMPLE XXXII

A mixture of 1.75 parts of 1-(2-methoxy-benzoyl)aziridine, 2.18 parts of 1,3-dihydro-1-(4-piperidinyl)-2H-benzimidazol-2-one, 1.6 parts of methanol and 10.8 parts of benzene is stirred and refluxed for 1.50 hours. The reaction mixture is cooled. After the addition of 2-propanone, the whole is acidified with ethanedioic acid. The formed ethanedioate salt is filtered off and crystallized from ethanol 70%, yielding 2.9 parts of N-{2-[4-(2,3-dihydro-2-oxo-1H-benzimidazol-1-yl)-1-piperidinyl] ethyl}-2-methoxybenzamide ethanedioate; mp. 217.4° C.

EXAMPLE XXXIII

A mixture of 1.5 parts of N-(2-bromoethyl)-2-nitrobenzamide, 1.55 parts of 5-chloro-1,3-dihydro-1-(4-piperidinyl)-2H-benzimidazol-2-one and 27 parts of N,N-dimethylformamide is stirred and refluxed for 5 hours. The reaction mixture is evaporated and the oily residue is crystallized from ethanol. The product is filtered off and dried, yielding 2.2 parts (67%) of N-{2-[4-(5-chloro-2,3-dihydro-2-oxo-1H-benzimidazol-1-yl)-1-piperidinyl] ethyl}-2-nitrobenzamide hydrobromide. hemihydrate; mp. 273.2° C.

EXAMPLE XXXIV

A mixture of 8.7 parts of 4-fluoro-N-{2-[4-(2,3-dihydro-2-oxo-1H-benzimidazol-1-yl)-1-piperidinyl] ethyl}-2-nitrobenzamide and 120 parts of methanol is hydrogenated at normal pressure and at room temperature with 2 parts of Raney-nickel catalyst. After the calculated amount of hydrogen is taken up, the catalyst is filtered off and the filtrate is evaporated. The residue is crystallized from a mixture of methanol and 2-propanol. The product is filtered off and dried, yielding 4.5 parts of 2-amino-N-{2-[4-(2,3-dihydro-2-oxo-1H-benzimidazol-1-yl)-1-piperidinyl] ethyl}-4-fluorobenzamide; mp. 229.3° C.

EXAMPLE XXXV

A mixture of 16 parts of N-{2-[4-(5-chloro-2,3-dihydro-2-oxo-1H-benzimidazol-1-yl)-1-piperidinyl] ethyl}-2-nitrobenzamide in 90 parts of tetrahydrofuran and 40 parts of methanol is hydrogenated at normal pressure and at room temperature with 3 parts of Raney-nickel catalyst. After the calculated amount of hydrogen is taken up, there is added a solution of methanol, previously saturated with gaseous ammonia. The catalyst is filtered off and the filtrate is evaporated. The residue is taken up in acidified water and the whole is washed twice with trichloromethane. The aqueous phase is separated and alkalized with a diluted sodium hydroxide solution. The product is extracted twice with trichloromethane. The combined extracts are washed three times with water, dried, filtered and evaporated. The residue is triturated in 2,2'-oxybispropane. The product is filtered off and crystallized from a mixture of ethanol and a small amount of water, yielding 2 parts of 2-amino-N-{2-[4-(5-chloro-2,3-dihydro-2-oxo-1H-benzimidazol-1-yl)-1-piperidinyl] ethyl}benzamide; mp. 226.8° C.

EXAMPLE XXXVI

A mixture of 5.3 parts of N-{2-[4-(2,3-dihydro-2-oxo-1H-benzimidazol-1-yl)-1-piperidinyl] ethyl}-2-methoxy-4-nitrobenzamide in 80 parts of methanol and 90 parts of tetrahydrofuran is hydrogenated at normal pressure and at room temperature with 5 parts of Raney-nickel catalyst. After the calculated amount of hydrogen is taken up, the catalyst is filered off and the filtrate is evaporated. The residue is crystallized from ethanol 96%, yielding 3.65 parts of 4-amino-N-{2-[4-(2,3-dihydro-2-oxo-1H-benzimidazol-1-yl)-1-piperidinyl] ethyl}-2-methoxybenzamide hydrate; mp. 220.6° C.

EXAMPLE XXXVII

A mixture of 1.68 parts of 1-(4-fluorobenzoyl)aziridine, 2.16 parts of 1,3-dihydro-1-(3,6-dihydro-1-(2H)pyridinyl)-2H-benzimidazol-2-one, 10.8 parts of benzene and 1.6 parts of methanol is stirred and refluxed for 1.50 hours. After cooling, the precipitated product is filtered off, washed with 2-propanone and crystallized from ethanol, yielding 1.76 parts of N-{2-[4-(2,3-dihydro-2-oxo-1H-benzimidazol-1-yl)-3,6-dihydro-1-(2H)-pyridinyl]ethyl}-4-fluorobenzamide; m.p. 202.7° C.

EXAMPLE XXXVIII

A mixture of 1.68 parts of 4-fluorobenzoyl chloride, 4.22 parts of 1-[1-(2-aminoethyl)-4-piperidinyl]-1,3-dihydro-2H-benzimidazol-2-one dihydrobromide, 4.83 parts of potassium carbonate and 18 parts of N,N-dimethylformamide is stirred overnight at 90° C. The reaction mixture is cooled, filtered over hyflo and the filtrate is washed with a small amount of N,N-dimethylformamide. The N,N-dimethylformamide is removed in vacuo and water is added to the residue. The product is extracted with trichloromethane. The extract is dried, filtered and evaporated. The residue is crystallized from 2-propanol, yielding 2.5 parts of N- {2-[4-(2,3-dihydro-2-oxo-1H-benzimidazol-1-yl)-1-piperidinyl] ethyl}-4-fluorobenzamide. mp. 231° C.

EXAMPLE XXXIX

A mixture of 0.74 parts of 1-(benzoyl)aziridine, 1.06 parts of 4-(4- chlorophenyl)-4-piperidinol, 5.4 parts of benzene and 0.4 parts of methanol is stirred and refluxed for 2 hours. The reaction mixture is cooled. Upon the addition of 1,1'-oxybisethane, the product is precipitated. After stirring for 15 minutes, the product is filtered off and dried, yielding 1.1 parts of N-{2-[4-(4-chlorophenyl)-4-hydroxy-1-piperidinyl] ethyl} benzamide; mp. 169° C.

EXAMPLE XL

A mixture of 0.84 parts of 1-(4-fluorobenzoyl)aziridine, 1.06 parts of 4(4-chlorophenyl)-4- piperidinol, 5.4 parts of benzene and 0.4 parts of methanol is stirred and refluxed for 2 hours. The reaction mixture is cooled and upon the addition of 1,1'-oxybisethane, the product is precipitated. The latter is filtered off and crystallized from ethyl acetate, yielding, after drying, 0.81 parts of N- {2-[4-(4-chlorophenyl)-4-hydroxy-1-piperidinyl]ethyl}-4-fluorobenazmide; mp. 168.7° C.

EXAMPLE XLI

A mixture of 0.96 parts of 1-(2- ethoxybenzoyl)aziridine, 1.06 parts of 4-(4-chlorophenyl)-4-piperidinol, 5.4 parts of benzene and 0.8 parts of methanol is stirred and refluxed for 2 hours. The reaction mixture is cooled. Upon the addition of 1,1'-oxybisethane, the product is precipitated. It is filtered off, crystallized from 2-propanol, filtered off again and dried overnight in vacuo at 80° C, yielding 1.4 parts of N-{2-[4-(4-chlorophenyl)-4-hydroxy-1-piperidinyl]ethyl}-2-ethoxybenzamide; mp. 171°–173° C.

EXAMPLE XLII

A mixture of 7.7 parts of 1-(2-thienylcarbonyl)aziridine, 10.8 parts of 4-(4- chlorophenyl)-4-piperidinol, 8 parts of methanol and 54 parts of benzene is stirred and refluxed for 1.50 hours. The reaction mixture is cooled and dissolved in trichloromethane. The solution is washed twice with water, dried, filtered and evaporated. The residue is crystallized from 2-propanone. The product is filtered off and dried, yielding 4.3 parts of N-{2-[4-(4-chlorophenyl)-4- hydroxy-1-piperidinyl]ethyl}-2-thiophenecarboxamide; mp. 153° C.

EXAMPLE XLIII

A mixture of 4.6 parts of 1(4-methylbenzoyl)aziridine, 4.23 parts of 4-(4-chlorophenyl)-4-piperidinol, 3.2 parts of methanol and 21.6 parts of benzene is stirred and refluxed for 1.50 hours. The reaction mixture is cooled to 0° C. The precipitated product is filtered off and washed with petroleumether. It is converted into the hydrochloride salt in 2-propanone and 2-propanol. The salt is filtered off and crystallized from ethanol. The product is filtered off and dried, yielding 3 parts of N-{2-[4-(4- chlorophenyl)-4-hydroxy-1-piperidinyl]ethyl}-4-methylbenzamide hydrochloride hydrate; m.p. 232.6° C.

EXAMPLE XLIV

A mixture of 7.6 parts of 1-(2-nitrobenzoyl)aziridine, 8.46 parts of 4-(4-chlorophenyl)-4-piperidinol, 43.2 parts of benzene and 6.4 parts of methanol is stirred and refluxed for 1.50 hours. The reaction mixture is cooled and the product is extracted with trichloromethane. The extract is washed three times with water, dried, filtered and evaporated. The residue is converted into the hydrochloride salt in 2-propanone. The salt is filtered off and crystallized from a mixture of ethanol and 2,2'-oxybispropane. The product is filtered off and dried, yielding 6parts of N-{2-[4-(4-chlorophenyl)-4-hydroxy-1-piperidinyl]ethyl}-2-nitrobenzamide hydrochloride; mp. 174.1° C.

EXAMPLE XLV

A mixture of 15 parts of 1-(4-fluoro-2-nitrobenzoyl)-aziridine, 11 parts of 4-(4-chlorophenyl)-4-piperidinol, 55.8 parts of benzene and 8.8 parts of methanol is stirred and refluxed for 1.50 hours. After stirring is continued overnight at room temperature, the reaction mixture is evaporated. The residue is dissolved in trichloromethane. The solution is washed with water and 8 parts of methanol are added. The whole is stirred for 10 minutes with silica gel. The latter is filtered off and the filtrate is evaporated. The residue is triturated with 2,2'-oxybis propane. The precipitated product is filtered off and crystallized from 4-methyl-2-pentanone. The product is filtered off and dried, yielding 9.5 parts of N-{2-[4-(4-chlorophenyl)-4- hydroxy-1-piperidinyl]ethyl}-4-fluoro-2-nitrobenzamide; mp. 144.3° C.

EXAMPLE XLVI

A mixture of 2.26 parts of 1-(2-bromobenzoyl)aziridine, 2.12 parts of 4-(4-chlorophenyl)-4-piperidinol, 10.8 parts of benzene and 0.8 parts of methanol is stirred and refluxed for 2 hours. The reaction mixture is cooled and evaporated. The residue is crystallized from ethyl acetate. The product is filtered off and dried, yielding 2.5 parts of 2-bromo-N-{2-[4-(4-chlorophenyl)-4-hydroxy-1-piperidinyl]ethyl} benzamide; mp. 120.6° C.

EXAMPLE XLVII

A mixture of 8 parts of 1-(4-fluoro-2-methoxybenzoyl)-aziridine, 3.7 parts of 4-(4-chlorophenyl)-4-piperidinol, 54 parts of benzene and 8 parts of methanol is stirred and refluxed for 1.50 hours. The reaction mixture is cooled to room temperature and 90 parts of benzene are added. The whole is washed with water and the layers are separated. The organic phase is dried, filtered and evaporated. The residue is crystallized from 2-propanone. The product is filtered off and dried, yielding 3.5 parts of N-{2-[4-(4-chlorophenyl)-4- hydroxy-1-piperidinyl]ethyl}-4-fluoro-2-methoxybenzamide; mp. 156.7° C.

EXAMPLE XLVIII

A mixture of 3.5 parts of N-{2-[4-(4-chlorophenyl)-4-hydroxy-1-piperidinyl]ethyl}-2-nitrobenzamide hydrochloride, 90 parts of tetrahydrofuran and 40 parts of methanol is hydrogenerated at normal pressure and at room temperature with 0.2 parts of platinium dioxide. After the calculated amount of hydrogen is taken up, the catalyst is filtered off and the filtrate is evaporated. The residue is converted into the hydrochloride salt in 2-propanol and 2,2'-oxybispropane. The salt is filtered off and dried, yielding 2.6 parts of 2-amino-N-{2-[4-(4-chlorophenyl)-4-hydroxy-1-piperidinyl]ethyl} benzamide dihydrochloride hemihydrate; mp. 195.7° C.

EXAMPLE XLIX

A mixture of 4.5 parts of N-{ 2-[4-(4-chlorophenyl)-4-hydroxy-1-piperidinyl]ethyl}-4-fluoro-2-nitrobenzamide, 40 parts of methanol and 90 parts of tetrahydrofuran is hydrogenated at normal pressure and at room temperature with 2 parts of Raney-nickel catalyst. After the calculated amount of hydrogen is taken up, the catalyst is filtered off and the filtrate is evaporated. The residue is converted into the hydrochloride salt in 2-propanol. The salt is filtered off and dried, yielding 2 parts of 2-amino-N-{2-[4-(4-chlorophenyl)-4-hydroxy-1-piperidinyl]ethyl}-4-fluorobenzamide dihydrochloride; mp. 210.7° C.

EXAMPLE L

Following the procedure of Example XI and using therein equivalent amounts of the appropriate starting materials, the following compounds are obtained in hydrochloride salt form:
N-{2-[1-(4-chlorophenyl)-4-oxo-1,3,8-triazaspiro[4,5]dec-8-yl]ethyl}-4-fluorobenzamide;
N-{2-[1-(4-chlorophenyl)-4-oxo-1,3,8-triazaspiro[4,5]-dec-8-yl]-ethyl} benzamide;
N-{2-[1-(4-bromophenyl)-4-oxo-1,3,8-triazaspiro[4,5]dec-8-yl]ethyl}-4-fluorobenzamide;

2-chloro-N-{2-[1-(4-chlorophenyl)-4-oxo-1,3,8-triazaspiro[4,5]-dec-8-yl]ethyl}-4-fluorobenzamide;
2-amino-N-{2-[1-(4-chlorophenyl)-4-oxo-1,3,8-triazaspiro[4,5]-dec-8-yl]ethyl}-4-fluorobenzamide; and
2-amino-N-{2-[1-(4-bromophenyl)-4-oxo-1,3,8-triazaspiro[4,5]-dec-8-yl]ethyl}-4-fluorobenzamide.

EXAMPLE LI

Following the procedure of Example XXII and using equivalent amounts of the appropriate starting materials, the following compounds of formula (I) are still prepared:
N-{2-[4-(5-bromo-2,3-dihydro-2-oxo-1H-benzimidazol-1-yl)-1-piperidinyl]ethyl}-4-fluorobenzamide;
N-{2-[4-(2,3-dihydro-5-methyl-2-oxo-1H-benzimidazol-1-yl)-1-piperidinyl]ethyl}-4-fluorobenzamide;
N-{2-[4-(5,6-dichloro-2,3-dihydro-2-oxo-1H-benzimidazol-1-yl)-1-piperidinyl]ethyl}-4-fluorobenzamide;
2-chloro-N-{2-[4-(5,6-dichloro-2,3-dihydro-2-oxo-1H-benzimidazol-1-yl)-1-piperidinyl]ethyl}-4-fluorobenzamide;
2-amino-N-{2-[4-(5-bromo-2,3-dihydro-2-oxo-1H-benzimidazol-1-yl)-1-piperidinyl]ethyl}-4-fluorobenzamide;
N-{2-[3,6-dihydro-4-(2,3-dihydro-2-oxo-1H-benzimidazol-1-yl)-1-(2H)-pyridinyl]ethyl}-benzamide;
2-amino-N-{2-[3,6-dihydro-4-(2,3-dihydro-2-oxo-1H-benzimidazol-1-yl)-1-(2H)-pyridinyl]ethyl}-4-fluorobenzamide;
2-chloro-N-{2-[3,6-dihydro-4-(2,3-dihydro-2-oxo-1H-benzimidazol-1-yl)-1-(2H)-pyridinyl]ethyl} -4-fluorobenzamide; and
N-{2-[4-(5-chloro-2,3-dihydro-2-oxo-1H-benzimidazol-1-yl)-1-(2H)-pyridinyl]ethyl} -4-fluorobenzamide.

EXAMPLE LII

Following the procedure of Example XL and using therein equivalent amounts of the appropriate starting materials, the following compounds are still obtained:
N-[2-{4-[4-chloro-3-(trifluoromethyl)phenyl]-4-hydroxy-1-piperidinyl} ethyl]-4-fluorobenzamide;
2-amino-[2-{4-[4-chloro-3-(trifluoromethyl)phenyl]-4-hydroxy-1-piperidinyl} ethyl]-4-fluorobenzamide;
2-chloro-[2-{4-[4-chloro-3-(trifluoromethyl)phenyl]-4-hydroxy-1-piperidinyl} ethyl]-4-fluorobenzamide;
N-{2-[4-(4-bromophenyl)-4-hydroxy-1-piperidinyl]ethyl}-4-fluorobenzamide; and
2-amino-N-{2-[4-(4-bromophenyl)-4-hydroxy-1-piperidinyl]-ethyl}-4-fluorobenzamide.

EXAMPLE LIII

To 230 parts of a solution of aziridine in water 0.875M are added 15 parts of sodium hydrogen carbonate while cooling at 0° C. Then there is added dropwise, during a 45 minutes-period, a solution of 42.5 parts of 5-chloro-2-methoxy-4-nitrobenzoyl chloride in 150 parts of trichloromethane at 0° C and while stirring vigorously. The mixture is diluted with about 150 parts of trichloromethane and the whole is stirred for 45 minutes without cooling. The reaction mixture is alkalized to pH 8 with a diluted sodium hydroxide solution. The product is extracted three times with trichloromethane. The combined extracts are washed three times with water, dried, filtered and evaporated, yielding 40 parts of 1-(5-chloro-2-methoxy-4-nitrobenzoyl)aziridine.

EXAMPLE LIV

To a stirred and cooled (ice-bath) mixture of 87 parts of 2-chloroethanamine hydrochloride and 300 parts of trichloromethane are added 224.2 parts of N,N-diethylethanamine, there is added dropwise, during a 1.50 hours period, a solution of 96 parts of 2-furancarbonyl chloride in 300 parts of trichloromethane at a temperature below 5° C. Upon completion, stirring is continued overnight at room temperature. The reaction mixture is poured onto water and the layers are separated. The aqueous phase is extracted with trichloromethane. The combined organic phases are washed with water, with a diluted hydrochloric acid solution and again twice with water, dried, filtered and evaporated. The residue is purified by column-chromatography over silica gel using a mixture of trichloromethane and 2% of methanol as eluent. The pure fractions are collected and the eluent is evaporated, yielding 95 parts of N-(2-chloroethyl)-2-furancarboxamide as a residue.

EXAMPLE LV

To a stirred and cooled mixture of 32 parts of 2-bromoethanamine hydrobromide in 150 parts of water is added a solution of 23.5 parts of 4-fluoro-2-nitrobenzoyl chloride in 54 parts of benzene. While cooling to 0°–5° C and while stirring vigourously, there is added dropwise a solution of 13 parts of sodium hydroxide in 200 parts of water (exothermic reaction). Upon completion, stirring is continued for 2 hours at 0°–10° C. The precipitated product is filtered off, washed with water and dried, yielding 30 parts (93.6%) of N-(2-bromoethyl)-4-fluoro-2-nitrobenzamide.

EXAMPLE LVI

To a stirred solution of 21 parts of sodium hydroxide in 75 parts of water is added a solution of 29 parts of 2-chloroethanamine hydrochloride in 75 parts of water. The whole is stirred and heated for 10 minutes at 90° C. After cooling to 0° C, 19 parts of sodium hydrogen carbonate are added. While stirring vigorously, there is added dropwise, during a 45 minutes-period, a solution of 49 parts of 2,5-dichlorobenzoyl chloride in 75 parts of trichloromethane at a temperature below 0° C. Upon completion, stirring is continued for 30 minutes without cooling. The reaction mixture is warmed to 25° C and adjusted to pH 8 with a diluted sodium hydroxide solution. The product is extracted three times with trichloromethane. The combined extracts are washed three times with water, dried filtered and evaporated, yielding 62 parts of 1-(2,5-dichlorobenzoyl)-aziridine as a residue.

EXAMPLE LVII

A mixture of 72 parts of methyl 2-pyridinecarboxylate and 32 parts of 2-aminoethanol is stirred and refluxed carefully for 2 hours. The reaction mixture is cooled and poured onto water. The product is extracted five times with trichloromethane. The combined extracts are dried, filtered and evaporated, yielding 49 parts of N-(2-hydroxyethyl)-2-pyridinecarboxamide as a residue.

To 49 parts of N-(2-hydroxyethyl)-2-pyridinecarboxamide are added dropwise 80 parts of sulfinyl chloride while stirring vigourously. Upon completion, stirring is continued first for 3 hours at reflux and further for 2 hours at room temperature. The excess of sulfinyl chloride is evaporated and the residue is poured onto hot methanol. After cooling, the precipitated product is filtered off (the filtrate is set aside) and washed thoroughly with 2,2'-oxybispropane, yielding a first fraction of 14 parts of N-(2-chloroethyl)-2-pyridinecarboxamide hydrochloride.

The filtrate (see above), which was set aside, is stirred with 2,2'-oxybispropane. The precipitated product is filtered off and dried, yielding a second fraction of 30 parts of N-(2-chloroethyl)-2-pyridinecarboxamide hydrochloride.

EXAMPLE LVIII

A mixture of 5.5 parts of methyl 1-methyl-1H-pyrrole-2-carboxylate and 2.4 parts of 2-aminoethanol is stirred and refluxed for 2 hours. The reaction mixture is evaporated till dry. Benzene is added twice to the residue and evaporation is continued each time till dry. The residue is purified by column-chromatography over silica gel using a mixture of trichloromethane and methanol (95:5 by volume) as eluent. The pure fractions are collected and the eluent is evaporated. The residue is taken up in petroleumether and upon scratching, the product solidifies. It is filtered off and dried, yielding 1.9 parts of N-(2-hydroxyethyl)-1-methyl-1H-pyrrole-2-carboxamide; mp. 78.1° C.

To a stirred solution of 40 parts of N-(2-hydroxyethyl)-1-methyl-1H-pyrrole-2-carboxamide in 450 parts of trichloromethane is added one drop of pyridine. Then there are added dropwise, during a 30 minutes-period, 28.3 parts of sulfinyl chloride (slightly exothermic reaction: temp. rises from 15° to 25° C). Upon completion, stirring is continued overnight at room temperature. The reaction mixture is evaporated and the residue is purified by column-chromatography over silica gel using a mixture of trichloromethane and methanol (96:4 by volume) as eluent. The pure fractions are collected and the eluent is evaporated. The residue is stirred in 2,2'-oxybispropane. The product is filtered off and dried, yielding 15 parts of N-(2-chloroethyl)-1-methyl-1H-pyrrole-2-carboxamide.

EXAMPLE LIX

A mixture of 12.94 parts of ethyl (2-bromoethyl)carbamate, 15.68 parts of 5-chloro-1,3-dihydro-1-(4-piperidinyl)-2H-benzimidazol-2-one, 10.08 parts of sodium hydrogen carbonate and 160 parts of ethanol is stirred and refluxed overnight. The formed precipitate is filtered off and washed with trichloromethane. The layers from the filtrate are separated. The organic phase is dried, filtered and evaporated. The residue is stirred in 2-propanone. The unreacted starting material is filtered off and the filtrate is purified by column-chromatography over silica gel using a mixture of trichloromethane and methanol (90:10 by volume) as eluent. The pure fractions are collected and the eluent is evaporated. The residue is crystallized from ethanol 70%. The product is filtered off and dried, yielding 6.5 parts of ethyl {2-[4-(5-chloro-2,3-dihydro-2-oxo-1H-benzimidazol-1-yl)-1-piperidinyl]-ethyl}carbamate; mp. 187.7° C.

A mixture of 6.6 parts of ethyl {2-[4-(5-chloro-2,3-dihydro-2-oxo-1H-benzimidazol-1-yl)-1-piperidinyl-]ethyl} -carbamate, 60 parts of a hydrobromic acid solution 48% in water and 4 parts of water is stirred and refluxed for 2.50 hours. After cooling, the precipitated product is filtered off and crystallized from water, yielding 5.5 parts of 1- [1-(2-aminoethyl)-4-piperidinyl]-5-chloro-1,3-dihydro-2H-benzimidazol-2-one dihydrobromide; mp. > 300° C.

EXAMPLE LX

A mixture of 38 parts of 1-(phenylmethyl)-4-piperidinamine, 40 parts of 2-chloronitrobenzene, 32 parts of sodium carbonate, a few crystals of potassium iodide in 320 parts of cyclohexanol is stirred and refluxed for 22 hours. After cooling, 300 parts of water are added. The organic layer is separated, diluted with 160 parts of water are added. The organic layer is separated, diluted with 160 parts of benzene and the whole is washed three times with 150 parts of water; the organic layer is dried over magnesium sulfate, filtered and evaporated. The residue is dissolved in a mixture of 40 parts of 2,2'-oxybispropane and 160 parts of hexane. After cooling to −15° C, the precipitate is filtered off and the filtrate is set aside. The precipitate is recrystallized from 160 parts of 2,2'-oxybispropane and filtered off, yielding 18.5 parts of N-(2-nitrophenyl)-1-(phenylmethyl)-4-piperidinamine; mp. 93.4°–94.6° C.

The combined mother liquors are diluted with 2,2'-oxybispropane and dry gaseous hydrogen chloride is introduced into it. The precipitated hydrochloride salt is filtered off. This crop is washed with 120 parts of water and the undissolved part is dried, yielding 18 parts of N-(2-nitrophenyl)-1-(phenylmethyl)-4-piperidinamine hydrochloride; mp. 206°–220° C (dec).

A solution of 31 parts of N-(2-nitrophenyl)-1-(phenylmethyl)-4-piperidinamine in 160 parts of tetrahydrofuran is hydrogenated at normal pressure and at a temperature of 40° C, with 20 parts of Raney nickel catalyst. After the calculated amount of hydrogen is taken up (3 moles) hydrogenation is stopped. The catalyst is filtered off and from the filtrate the solvent is evaporated. The solid residue is washed with 160 parts of 2,2'-oxybispropane, to yield 22 parts of N-[1-(phenylmethyl)-4-piperidinyl]-1,2-benzenediamine; mp. 112°–113° C. On concentrating the filtrate to about one quarter of its volume a second crop of 2.5 parts of N-[1-(phenylmethyl)-4-piperidinyl]-1,2-benzenediamine is obtained; mp. 108°–109° C.

A mixture of 5 parts of N-[1-(phenylmethyl)-4-piperidinyl]-1,2-benzenediamine, 2.35 parts of methyl (iminomethoxymethyl)carbamate, 5 parts of acetic acid and 75 parts of trichloromethane is stirred and refluxed for 48 hours. The reaction mixture is evaporated and the residue is taken up in water. The solution is neutralized with ammonium hydroxide solution. The precipitated product is purified by column-chromatography over silica gel using a mixture of trichloromethane and methanol (95:5 by volume) as eluent. The pure fractions are collected and the eluent is evaporated, yielding 1.75 parts of methyl {1,3-dihydro-1-[1-(phenylmethyl)-4-piperidinyl]-2H-benzimidazol-2-ylidene} carbamate; mp. 169.7° C.

A mixture of 3.64 parts of methyl {2,3-dihydro-1-[1-(phenylmethyl)-4-piperidinyl]-1H-benzimidazol-2-ylidene}carbamate, 24 parts of a hydrochloric acid solution and 40 parts of ethanol is stirred and refluxed overnight. The reaction mixture is evaporated and the residue is dissolved in water. This solution is alkalized with a concentrated ammonium hydroxide solution. The precipitated product is filtered off, washed with water and dissolved in trichloromethane. The solution is dried, filtered and evaporated, yielding 2.1 parts of 1-[1-(phenylmethyl)-4-piperidinyl]-1H-benzimidazol-2-amine as a residue.

A mixture of 2 parts of 1-[1-(phenylmethyl)-4-piperidinyl]-1H-benzimidazol-2-amine, 3 parts of acetic acid anhydride and 45 parts of methylbenzene is stirred and refluxed for 3 hours. The reaction mixture is evaporated and water is added to the residue. The whole is alkalized with a concentrated ammonium hydroxide solution. The precipitated product is filtered off, washed with water and dissolved in trichloromethane. The solution is dried, filtered and evaporated. The residue is crystallized from 2,2'-oxybispropane, yielding, after drying, 0.8 parts of N-{1,3-dihydro-1-[1-(phenylmethyl)-4-piperidinyl]-2H-benzimidazol-2-ylidene} acetamide; mp. 189.2° C.

A mixture of 12 parts of N-{1,3-dihydro-1-[1-(phenylmethyl)-4-piperidinyl]-2H-benzimidazol-2-ylidene} acetamide and 120 parts of methanol is hydrogenated at normal pressure and at room temperature with 5 parts of palladium-on-charcoal catalyst 10%. After the calculated amount of hydrogen is taken up, the catalyst is filtered off over hyflo and the filtrate is evaporated. The residue is crystallized from a mixture of 2,2'-oxybispropane and 2-propanol. The product is filtered off and recrystallized from a mixture of ethanol and 2,2'-oxybispropane, yielding 2.6 parts of N-[1,3-dihydro-1-(4-piperidinyl)-2H-benzimidazol-2-ylidene]acetamide; mp. 164.5° C.

EXAMPLE LXI

A mixture of 1.82 parts of (1-aziridinyl) (3-chlorophenyl) methanone, 2.32 parts of 1-phenyl-1,3,8-triazaspiro[4,5]decan-4-one, 10.8 parts of benzene and 1.6 parts of methanol is stirred and refluxed for 1.50 hours. The reaction mixture is cooled and diluted with 2-propanone. The solution is acidified with 2-propanol, previously saturated with gaseous hydrogen chloride. The formed hydrochloride salt is filtered off and crystallized from a mixture of ethanol and water (7:3 by volume), yielding, after drying, 1.8 parts of 3-chloro-N-[2-(4-oxo-1-phenyl-1,3,8-triazaspiro[4,5]-dec-8-ylethyl]benzamidehydrochloride; mp. 263.4° C.

EXAMPLE LXII

Following the procedure of example LXI and using equivalent amounts of the appropriate starting materials and following compounds are prepared in free base form, or in the form of an acid addition salt after treatment of the base with the appropriate acid.
N-[2-(4-oxo-1-phenyl-1,3,8-triazaspiro[4,5]dec-8-yl)ethyl]-3-(trifluoromethyl)benzamide hydrochloride; mp. 262° C;
3-fluoro-N-[2-(4-oxo-1-phenyl-1,3,8-triazaspiro[4,5]-dec-8-yl)ethyl]-benzamide hydrochloride; mp. 248.5° C;
3,4,5-trimethoxy-N-[2-(4-oxo-1-phenyl-1,3,8-triazaspiro[4,5]dec-8-yl)ethyl]benzamide hydrochloride; mp. 271.6° C;
2,5-dichloro-N-{2-[1-(4-fluorophenyl)-4-oxo-1,3,8-triazaspiro[4,5]-dec-8-yl]ethyl} benzamide hydrochloride; mp. 234.8° C.
N-{2-[1-(4-fluorophenyl)-4-oxo-1,3,8-triazaspiro[4,5]dec-8-yl]ethyl}-3-methoxybenzamide hydrochloride; mp. 243.2° C;
2,5-dichloro-N-[2-(4-oxo-1-phenyl-1,3,8-triazaspiro[4,5]dec-8-yl)ethyl]-benzamide hydrochloride; mp. 249.8° C;
4-fluoro-2-methoxy-N-[2-(4-oxo-1-phenyl-1,3,8-triazaspiro[4,5]dec-8-yl)ethyl]benzamide; mp. 193.8° C;
5-chloro-2-methoxy-4-nitro-N-[2-(4-oxo-1-phenyl-1,3,8-triazaspiro-[4,5]dec-8-yl)ethyl]benzamide hydrochloride hemihydrate hemiethanolate; mp. 176.5° C;
3-methyl-N-[2-(4-oxo-1-phenyl-1,3,8-triazaspiro[4,5]-dec-8-yl)ethyl]-benzamide ethanedioate; mp. 225.3° C;
N-{2-[1-(4-fluorophenyl)-4-oxo-1,3,8-triazaspiro[4,5]dec-8-yl]ethyl}-3-methylbenzamide ethanedioate; mp. 225.6° C;
5-chloro-N-{2-[1-(4-fluorophenyl)-4-oxo-1,3,8-triazaspiro[4,5]dec-8-yl]ethyl}-2-methoxybenzamide; mp. 242.2° C;
5-chloro-N-{2-[1-(4-fluorophenyl)-4-oxo-1,3,8-triazaspiro[4,5]dec-8-yl]ethyl}-2-methoxy-4-nitrobenzamide.hydrochloride hemihydrate; mp. 226.2° C; and
3-methoxy-N-[2-(4-oxo-1-phenyl-1,3,8-triazaspiro[4,5]dec-8-yl)ethyl]-benzamide hydrochloride; mp. 251° C.

EXAMPLE LXIII

A member of 6.9 parts of N-(2-chloroethyl)-2-furancarboxamide, 9.2 parts of 1-phenyl-1,3,8-triazaspiro[4,5]decan-4-one, 6.6 parts of potassium iodide and 135 parts of N,N-dimethylformamide is stirred first for 3 hours at reflux and further overnight at room temperature. The reaction mixture is evaporated and the residue is taken up in water. The whole is alkalized and the product is extracted with 4-methyl-2-pentanone. The extract is dried, filtered and evaporated. The residue is purified by column-chromatography over silica gel using a mixture of trichloromethane and methanol (96:4 by volume) as eluent. The pure fractions are collected and the eluent is evaporated. The solid residue is crystallized from 2-propanone. The product is filtered off and dried, yielding 1.9 parts of N-[2-(4-oxo-1-phenyl-1,3,8-triazaspiro [4,5]dec-8-yl)ethyl]-2-furancarboxamide; mp. 196.3° C.

EXAMPLE LXIV

Following the procedure of example LXIII there is prepared N-{2-[1-(4-fluorophenyl)-4-oxo-1,3,8-triazaspiro[4,5]dec-8-yl]-ethyl}-2-furancarboxamide hydrochloride; mp. 254.2° C by the reaction of N-(2-chloroethyl)-2-furancarboxamide with 1-(4-fluorophenyl)-1,3,8-triazaspiro[4,5]decan-4-one.

EXAMPLE LXV

A mixture of 4.4 parts of N-(2-chloroethyl)-2-pyridinecarboxamide, 13.8 parts of 1-phenyl-1,3,8-triazaspiro[4,5]decan-4-one, 3.3 parts of potassium iodide and 200 parts of 4-methyl-2-pentanone is stirred and refluxed for 24 hours. The reaction mixture is evaporated and the residue is purified by column-chromatography over silica gel using a mixture of trichloromethane and methanol (98:2 by volume) as eluent. The pure fractions are collected and the eluent is evaporated. The residue is converted into the hydrochloride salt in 2-propanol. The salt is filtered off and crystallized from ethanol, yielding 1.1 parts of N-[2-(4-oxo-1-phenyl-1,3,8-triazaspiro[4,5]dec-8-yl)ethyl]-2-pyridinecarboxamide dihydrochloride hydrate; mp. 250.5° C.

EXAMPLE LXVI

A mixture of 3.75 parts of N-(2-chloroethyl)-1-methyl-1H-pyrrole-2-carboxamide, 5 parts of 1-(4-fluorophenyl)-1,3,8-triazaspiro[4,5]decan-4-one, 1.7 parts of sodium hydrogen carbonate, 0.1 parts of potassium iodide and 160 parts of 4-methyl-2-pentanone is stirred and refluxed for 48 hours. The reaction mixture is cooled and the solvent is evaporated. The residue is purified by column-chromatography over silica gel using a mixture of trichloromethane and methanol (95:5 by volume) as eluent. The pure fractions are collected and the eluent is evaporated. The residue is converted into the hydrochloride salt in 2-propanol and 2,2'-oxybispropane. The salt is filtered off and crystallized from methanol, yielding 0.8 parts of N-{2-[1-(4-fluorophenyl)-4-oxo-1,3,8-triazaspiro[4,5]dec-8-yl]ethyl}-1-methyl-1H-pyrrole-2-carboxamide hydrochloride; mp. 273.4° C.

EXAMPLE LXVII

A mixture of 6 parts of 5-chloro-2-methoxy-4-nitro-N-[2-(4-oxo-1-phenyl-1,3,8-triazaspiro[4,5]dec-8-yl)ethyl]benzamide in 150 parts of acetic acid is hydrogenated at normal pressure and at room temperature with 1 part of Raney-nickel catalyst. After the calculated amount of hydrogen is taken up, the catalyst is filtered off and the filtrate is evaporated. The residue is taken up in water and the whole is alkalized. The precipitated product is filtered off and crystallized twice from ethanol, yielding 1.7 parts of 4-amino-5-chloro-2-methoxy-N-[2-(4-oxo-1-phenyl-1,3,8-triazaspiro[4,5]-dec-8-yl)ethyl]benzamide; mp. 247.4° C.

EXAMPLE LXVIII

Following the procedure of Example LXVII and using therein 5-chloro-N-{2-[2-[1-(4-fluorophenyl)-4-oxo-1,3,8-triazaspiro[4,5[-dec-8-yl]ethyl}-2-methoxy-4-nitrobenzamide as a starting material and after converting the product thus obtained into a hydrochloride salt there is prepared: 4-amino-5-chloro-N-{2-[1-(4-fluorophenyl)-4-oxo-1,3,8-triazaspiro[4,5]dec-8-yl]ethyl}-2-methoxybenzamide hydrochloride; mp. 239.8° C.

EXAMPLE LXIX

A mixture of 9 parts of N-{2-[1-(4-fluorophenyl)-4-oxo-1,3,8-triazaspiro[4,5]dec-8-yl]ethyl}-2-nitrobenzamide hydrochloride in 150 parts of acetic acid is hydrogenated at normal pressure and at room temperature with 2 parts of palladium-on-charcoal catalyst 10%. After the calculated amount of hydrogen is taken up, the catalyst is filtered off and the filtrate is evaporated. The residue is taken up in water and the whole is alkalized with ammonium hydroxide. The product is extracted twice with trichloromethane. The combined extracts are washed twice with water, dried, filtered and evaporated. The solid residue is boiled with 2-propanol and filtered. The product is allowed to crystallize from the filtrate. It is filtered off and dried in vacuo, yielding 5 parts of 2-amino-N-{2-[1-(4-fluorophenyl)-4-oxo-1,3,8-triazaspiro[4,5]dec-8-yl]ethyl} benzamide; mp. 194.9° C.

EXAMPLE LXX

A mixture of 9 parts of 2-amino-4-fluoro-N-{2-[1-(4-fluorophenyl)-4-oxo-1,3,8-triazaspiro [4,5]dec-8-yl]ethyl}-benzamide, 8.5 parts of acetic acid anhydride and 85 parts of water is stirred for 30 minutes in a water-bath at about 80° C. The reaction mixture is cooled and alkalized with ammonium hydroxide. The product is extracted with trichloromethane. The aqueous phase is separated and extracted with trichloromethane. The combined organic phases are washed three times with water, dried, filtered and evaporated. The residue is crystallized from 2-propanol. The product is filtered off and dried, yielding 5.2 parts of 2-(acetylamino)-4-fluoro-N-{2-[1-(4-fluorophenyl)-4-oxo-1,3,8-triazaspiro-[4,5]dec-8-yl]ethyl}benzamide; mp. 195.1° C.

EXAMPLE LXXI

A mixture of 1.68 parts of (1-aziridinyl) (3-fluorophenyl) methanone, 2.18 parts of 1,3-dihydro-1-(4-piperidinyl)-2H-benzimidazol-2-one, 10.8 parts of benzene and 1.6 parts of methanol is stirred and refluxed for 1.50 hours. The reaction mixture is cooled, the precipitated product is filtered off and crystallized from ethanol, yielding 1.75 parts of N-{2-[2-(2,3-dihydro-2-oxo-1H-benzimidazol-1-yl)-1-piperidinyl]ethyl}-3-fluorobenzamide; mp. 226.3° C.

EXAMPLE LXXII

Following the procedure of Example LXXI and using equivalent amounts of the appropriate starting materials the following compounds are obtained in free base form or in the form of an acid addition salt after treatment of the base with the appropriate acid:

N-{2-[4-(2,3dihydro-2-oxo-1H-benzimidazol-1-yl)-1-piperidinyl]-ethyl}-2,6-dimethylbenzamide; mp. 208.1° C;

3-chloro-N-{2-[4-(2,3-dihydro-2-oxo-1H-benzimidazol-1-yl)-1-piperidinyl]ethyl}benzamide ethanolate; mp. 226.5° C;

N-{2-[4-(2,3-dihydro-2-oxo-1H-benzimidazol-1-yl)-1-piperidinyl]-ethyl}-3-(trifluoromethyl)benzamide; mp. 225.7° C;

N-{2-[4-(2,3-dihydro-2-oxo-1H-benzimidazol-1-yl)-1-piperidinyl]-ethyl}-3,4,5-trimethoxybenazmide; mp. 248.1° C;

5-chloro-N-{2-[4-(5-chloro-2,3-dihydro-2-oxo-1H-benzimidazol-1-yl)-1-piperidinyl]ethyl}-2-methoxybenzamide; mp. 241.8° C;

N-{2-[4-(2,3-dihydro-2-oxo-1H-benzimidazol-1-yl)-1-piperidinyl]-ethyl}-3-methylbenzamide ethanedioate; mp. 228.8° C;

N-{2-[4-(2,3-dihydro-2-oxo-1H-benzimidazol-1-yl)-1-piperidinyl]-ethyl}-3-methoxybenzamide ethanedioate; mp. 220° C;

2,5-dichloro-N-{2-[4-(2,3-dihydro-2-oxo-1H-benzimidazol-1-yl)-1-piperidinyl]ethyl}-benzamide hydrochloride; mp. 245.6°–250.2° C;

N-{2-[4-(5-chloro-2,3-dihydro-2-oxo-1H-benzimidazol-1-yl)-1-piperidinyl]ethyl}-3-methoxybenzamide hydrochloride; mp. 236.3° C;

5-chloro-N-{2-[4-(2,3-dihydro-2-oxo-1H-benzimidazol-1-yl)-1-piperidinyl]ethyl}-2-methoxy-4-nitrobenzamide; mp. 226° C;

N-[2-{4-[2-(acetylimino)-2,3-dihydro-1H-benzimidazol-1-yl}-1-piperidinyl}ethyl]-4-fluorobenzamide; mp. 216.9° C; and 5-chloro-N-{2-[4-(5-chloro-2,3-dihydro-2-oxo-1H-benzimidazol-1-yl)-1-piperidinyl]ethyl}-2-methoxy-4-nitrobenzamide; mp. 223.6° C.

EXAMPLE LXXIII

A mixture of 1.68 parts of 1-(4-fluorobenzoyl)aziridine, 3.07 parts of 2,3-dihydro-2-oxo-3-(4-piperidinyl)-1H-benzimidazole-1-propanenitrile hydrochloride, 1.65 parts of N,N-diethylethanamine, 10.8 parts of benzene and 1.6 parts of methanol is stirred and refluxed for 1.50 hours. The reaction mixture is cooled and poured onto water. The product is extracted with trichloromethane. The extract is dried, filtered and evaporated. The residue is crystallized from 2-propanol. The product is filtered off and recrystallized from 2-propanol, yielding 1 part of N-[2-{4-[3-(2-cyanoethyl)-2,3-dihydro-2-oxo-1H-benzimidazol-1-yl]-1-piperidinyl}ethyl]-4-fluorobenzamide; mp. 172.2° C.

EXAMPLE LXXIV

A mixture of 5.6 parts of N-(2-chloroethyl)-1-methyl-1H-pyrrole-2-carboxamide, 6.52 parts of 1,3-dihydro-1-(4-piperidinyl)-2H-benzimidazol-2-one, 2.52 parts of sodium hydrogen carbonate, 0.1 parts of potassium iodide and 240 parts of 4-methyl-2-pentanone is stirred and refluxed for 62 hours. The reaction mixture is cooled and the solvent is evaporated. The residue is purified by columnchromatography over silica gel using a mixture of trichloromethane and methanol (95:5 by volume) as eluent. The pure fractions are collected and the eluent is evaporated. The residue is converted into the hydrochloride salt in ethanol, 2-propanol and 2,2'-oxybispropane. The salt is filtered off and crystallized from a mixture of ethanol and 2,2'-oxybispropane, yielding 0.6 parts of N-{2-[4-(2,3-dihydro-2-oxo-1H-benzimidazol-1-yl)-1-piperidinyl]ethyl}-1-methyl-1H-pyrrole-2-carboxamide hydrochloride hydrate; mp. 237.7° C.

EXAMPLE LXXV

A mixture of 8.8 parts of N-(2-chloroethyl)-3-pyridinecarboxamide hydrochloride, 4.6 parts of 1,3-dihydro-1-(4-piperidinyl)-2H-benzimidazol-2-one, 4.24 parts of sodium carbonate and 120 parts of 4-methyl-2-pentanone is stirred and refluxed for 48 hours. The reaction mixture is cooled to room temperature and poured onto water. The product is extracted five times with trichloromethane. The combined extracts are dried, filtered and evaporated. The residue is purified by column-chromatography over silica gel using a mixture of trichloromethane and methanol (90:10 by volume) as eluent. The pure fractions are collected and the eluent is evaporated. The residue is converted into the hydrochloride salt in ethanol and 2-propanol. The salt is filtered off and crystallized from a mixture of methanol and ethanol. It is filtered off again and recrystallized from a mixture of ethanol and 2,2'-oxybispropane, yielding 0.8 parts of N-{2-[4-(2,3-dihydro-2-oxo-1H-benzimidazol-1-yl)-1-piperidinyl]ethyl}-3-pyridinecarboxamide dihydrochloride hydrate; mp. 214.1° C.

EXAMPLE LXXVI

A mixture of 7.3 parts of N-(2-bromoethyl)-4-fluoro-2-nitrobenzamide, 6.2 parts of 5-chloro-1,3-dihydro-1-(4-piperidinyl)-2H-benzimidazol-2-one, 5.2 parts of sodium carbonate and 80 parts of 4-methyl-2-pentanone is stirred and refluxed overnight. The reaction mixture is cooled, water is added and the layers are separated. The aqueous phase is extracted with 4-methyl-2-pentanone. The combined organic phases are washed with water, dried, filtered and evaporated. The residue is purified by column-chromatography over silica gel using a mixture of trichloromethane and methanol (90:10 by volume) as eluent. The pure fractions are collected and the eluent is evaporated. The oily residue is crystallized from 2-propanone. The product is filtered off and dried, yielding 1 part of N-{2-[4-(5-chloro-2,3-dihydro-2-oxo-1H-benzimidazol-1-yl)-1-piperidinyl]-ethyl}-4-fluoro-2-nitrobenzamide.

EXAMPLE LXXVII

A mixture of 16 parts of N-(2-bromoethyl)-4-fluoro-2-nitrobenzamide, 12.6 parts of 5-chloro-1,3-dihydro-1-(4-piperidinyl)-2H-benzimidazol-2-one and 216 parts of N,N-dimethylformamide is stirred and refluxed for 3 hours. The N,N-dimethylformamide is evaporated and the residue is purified by column-chromatography over silica gel using a mixture of trichloromethane and methanol (95:5 by volume) as eluent. The pure fractions are collected and the eluent is evaporated. The residue is converted into the hydrochloride salt in 2-propanone and 2-propanol. The salt is filtered off and crystallized from methanol, yielding 1.5 parts of N-{2-[4-(5-chloro-2,3-dihydro-2-oxo-1H-benzimidazol-1-yl)-1-piperidinyl]ethyl}-4-fluoro-2-nitrobenzamide hydrochloride; mp. 276.8° C.

EXAMPLE LXXVIII

A mixture of 2.2 parts of N-(2-chloroethyl)-2-pyridinecarboxamide hydrochloride, 6.6 parts of 1,3-dihydro-1-(4-piperidinyl)-2H-benzimidazol-2-one, 1.66 parts of potassium iodide and 120 parts of 4-methyl-2-pentanone is stirred and refluxed overnight. After cooling, the precipitated product is filtered off and dissolved in water. The solution is alkalized with sodium carbonate and the product is extracted three times with 4-methyl-2-pentanone. The combined extracts are washed with water, dried, filtered and evaporated. The residue is purified by column-chromatography over silica gel using a mixture of trichloromethane and methanol (95:5 by volume) as eluent. The pure fractions are collected and the element is evaporated. The residue is converted into the hydrochloride salt in 2-propanone and 2-propanol. The salt is filtered off and crystallized from a mixture of ethanol and 2,2'-oxybispropane (1:1 by volume), yielding 2 parts of N-{2-[4-(2,3-dihydro-2-oxo-1H-benzimidazol-1-yl)-1-piperidinyl]-ethyl}-2-pyridinecarboxamide dihydrochloride dihydrate; mp. 165.7° C.

EXAMPLE LXXIX

A mixture of 6.9 parts of N-(2-chloroethyl)-2-furancarboxamide, 9.8 parts of 1,3-dihydro-1-(4-piperidinyl)-2H-benzimidazol-2-one, 6.6 parts of potassium iodide and 135 parts of N,N-dimethylformamide is stirred first for 3 hours at reflux and further overnight at room temperature. The reaction mixture is evaporated. The residue is taken up in water and the whole is alkalized. The product is extracted with 4-methyl-2-pentanone. The layers are separated and the aqueous phase is set aside. The organic phase is washed with water, dried, filtered and evaporated. The solid residue is crystallized from 2-propanone. The product is filtered off and dried, yielding a first fraction of 1 part of N-{2-[4-(2,3-dihydro-2-oxo-1H-benzimidazol-1-yl)-1-piperidinyl]ethyl}-2-furancarboxamide; mp. 228.9° C. The aqueous phase, which was set aside (see above), is allowed to stand overnight. The precipitated product is filtered off and crystallized from methanol, yielding a second fraction of 4 parts of N-{2-[4-(2,3-dihydro-2-oxo-1H-benzimidazol-1-yl)-1-piperidinyl]ethyl}-2-furancarboxamide; mp. 231.7° C.

EXAMPLE LXXX

A mixture of 4.2 parts of 5-chloro-N-{2-[4-(2,3-dihydro-2-oxo-1H-benzimidazol-1-yl)-1-piperidinyl]ethyl}-2-methoxy-4-nitrobenzamide in 150 parts of acetic acid is hydrogenated at normal pressure and at room temperature with 1 part of Raney-nickel catalyst. After the calculated amount of hydrogen is taken up, the catalyst is filtered off and the filtrate is evaporated. Water is added to the residue and the whole is alkalized with a diluted sodium hydroxide solution. The precipitated product is filtered off and crystallized from methanol. The product is filtered off (the filtrate is set aside) and dried, yielding a first fraction of 0.8 parts of 4-amino-5-chloro-N-{2-[4-(2,3-dihydro-2-oxo-1H-benzimidazol-1-yl)-1-piperidinyl]ethyl}-2-methoxybenzamide; mp. 230.1° C.

The filtrate, which was set aside, is concentrated. A second fraction is filtered off, yielding 1.6 parts of 4-amino-5-chloro-N-{2-[4-(2,3-dihydro-2-oxo-1H-benzimidazol-yl)-1-piperidinyl]ethyl}-2-methoxybenazmide; mp. 232.5° C.

EXAMPLE LXXXI

A mixture of 4.5 parts of N-{2-[4-(2,3-dihydro-2-oxo-1H-benzimidazol-1-yl)-1-piperidinyl]ethyl}-2-nitrobenzamide, 80 parts of methanol and 45 parts of tetrahydrofuran is hydrogenated at normal pressure and at room temperature with 2 parts of Raney-nickel catalyst. After the calculated amount of hydrogen is taken up, the catalyst is filtered off and the filtrate is evaporated. The residue is crystallized twice from 2-propanol. The product is filtered off and dried, yielding 2 parts of 2-amino-N-{2-[4-(2,3-dihydro-2-oxo-1H-benzimidazol-1-yl)-1-piperidinyl]ethyl}benzamide hemihydrate; mp. 219.2° C.

EXAMPLE LXXXII

A mixture of 1 part of 2-amino-N-{2-[4-(2,3-dihydro-2-oxo-1H-benzimidazol-1-yl)-1-piperidinyl]ethyl}-4-fluorobenzamide, 1 part of acetic acid anhydride and 15 parts of water is stirred for 30 minutes in a water-bath at 80°–90° C. The reaction mixture is cooled and alkalized with an ammonium hydroxide solution. The product is extracted with trichloromethane. The extract is dried, filtered and evaporated. The residue is crystallized from 4-methyl-2-pentanone. The product is filtered off and dried, yielding 0.5 parts of 2-(acetylamino)-N-{2-[4-(2,3-dihydro-2-oxo-1H-benzimidazol-1-yl)-1-piperidinyl]ethyl}-4-fluorobenzamide; mp. 210° C.

EXAMPLE LXXXIII

A mixture of 0.9 parts of N-{2-[4-(5-chloro-2,3-dihydro-2-oxo-1H-benzimidazol-1-yl) - 1 - piperidinyl]ethyl}-4-fluoro-2-nitrobenzamide in 80 parts of methanol is hydrogenated at normal pressure and at room temperature with 1 part of Raney-nickel catalyst. After the calculated amount of lhydrogen is taken up, the catalyst is filtered off and the filtrate is evaporated. The residue is converted into the hydrochloride salt in 4-methyl-2-pentanone and 2-propanol. The salt is filtered off and crystallized from a mixture of 2-propanone and water, yielding 0.2 parts of 2-amino-N-{2-[4-(5-chloro-2,3-dihydro-2-oxo- 1-yl)-1-piperidinyl]ethyl}-4-fluorobenzamide hydrochloride dihydrate; mp. 250° C.

EXAMPLE LXXXIV

A mixture of 0.8 parts of 2-amino-N-{2-[4-(5-chloro-2,3-dihydro-2-oxo-1H-benzimidazol-1-yl)-1-piperidinyl]ethyl}-4-fluorobenzamide, 1 part of acetic acid anhydride and 10 parts of water is stirred for 30 minutes in a water-bath at 80°–90° C. The reaction mixture is cooled, alkalized with ammonium hydroxide and the product is extracted with trichloromethane. The extract is dried, filtered and evaporated. The residue is purified by column-chromatography over silica gel using a mixture of trichloromethane and methanol (95:5 by volume) as eluent. The pure fractions are collected and the eluent is evaporated, yielding 0.5 parts of 2-(acetylamino)-N-{2-[4-(5-chloro-2,3-dihydro-2-oxo-1H-benzimidazol-1-yl)-1-piperidinyl]ethyl}-4-fluorobenzamide; mp. 196.5° C.

EXAMPLE LXXXV

A mixture of 1.76 parts of 1-(2,6-dimethylbenzoyl)aziridine, 1.06 parts of 4-(4-chlorophenyl)-4-piperidinol, 10.8 parts of benzene and 1.6 parts of methanol is stirred and refluxed for 2 hours. After cooling, the reaction mixture is evaporated. The residue is converted into the cyclohexylsulfamate salt in ethyl acetate. The salt is filtered off and crystallized from a small amount of 2-propanol. The product is filtered off and dried at 50° C, yielding 1.5 parts of N-{2-[4-(4-chlorophenyl)-4-hydroxy-1-piperidinyl]ethyl}-2,6-dimethylbenzamide cyclohexylsulfamate; mp. 236°–280° C (dec.).

EXAMPLE LXXXVI

Following the procedure of Example LXXXV and using equivalent amounts of the appropriate starting materials the following compounds are obtained in free base form or in the form of an acid additions salt after treatment of the base with the appropriate acid:

N-{2-[4-(4-chlorophenyl)-4-hydroxy-1-piperidinyl]ethyl}-3-methylbenzamide ethanedioate; mp. 181.2° C;

2,5-dichloro-N-{2-[4-(4-chlorophenyl)-4-hydroxy-1-piperidinyl]-ethyl}benzamide hydrochloride, hydrate; mp. 187.5° C;

N-{2-[4-(4-chlorophenyl)-4-hydroxy-1-piperidinyl]ethyl}-3-methoxybenzamide ethanedioate, hemi-2-propanolate; mp. 183.4° C;

5-chloro-N-{2-[4-(4-chlorophenyl)-4-hydroxy-1-piperidinyl]ethyl}-2-methoxy-4-nitrobenzamide methanolate; mp. 163.1° C; and N-[2-{4[4-chloro-3-(trifluoromethyl)phenyl]-4-hydroxy-1-piperidinyl}-ethyl]-4-fluorobenzamide dicyclohexylsulfamate.

EXAMPLE LXXXVII

A mixture of 5.8 parts of 2-amino-N-{2-[4-(4-chlorophenyl)-4-hydroxy-1-piperidinyl]ethyl}-4-fluorobenzamide, 5.5 parts of acetic acid anhydride and 55 parts of water is stirred and heated for 30 minutes in a water-bath at about 80° C. The reaction mixture is cooled and alkalized with ammonium hydroxide. The product is extracted with trichloromethane. The aqueous phase is separated and extracted with trichloromethane. The combined organic phases are washed three times with water, dired, filtered and evaporated. The oily residue is crystallized from 4-methyl-2-pentanone. The product is filtered off and dried, yielding 4.5 parts of 2-(acetylamino)-N-{2-[4-(4-chlorophenyl)-4-hydroxy-1-piperidinyl]ethyl}-4-fluorobenzamide; mp. 175.1° C.

EXAMPLE LXXXVIII

A mixture of 10.6 parts of N-(2-bromoethyl)-2-nitrobenzamide, 9.2 parts of A(±)-4-(4-chlorophenyl)-3-methyl-4-piperidinol and 270 parts of N,N-dimethylformamide is stirred and refluxed for 4 hours. The reaction mixture is evaporated till dry. The residue is purified by column-chromatography over silica gel using a mixture of trichloromethane and methanol (95:5 by volume) as eluent. The pure fractions are collected and the eluent is evaporated. The residue is converted into the hydrochloride salt is 2-propanol. The salt is filtered off and crystallized from a mixture of ethanol and 2,2'-oxybispropane (1:1 by volume). The product is filtered off and dried overnight at 60° C, yielding 4.5 parts of A-(±)-N-{2-[4-(4-chlorophenyl)-4-hydroxy-3-methyl-1-piperidinyl]ethyl}-2-nitrobenzamide hydrochloride; mp. 228° C.

EXAMPLE LXXXIX

Following the procedure of Example LXXXVIII and using therein an equivalent amount of N-(2-bromoethyl)-4-fluoro-2-nitrobenzamide in place of the N-(2-bromoethyl)-2-nitrobenzamide used therein there is prepared:
A-(±)-N-{2-[4-(4-chlorophenyl)-4-hydroxy-3-methyl-1-piperidinyl]-ethyl}-4-fluoro-2-nitrobenzamide hydrochloride

EXAMPLE XC

A mixture of 2.8 parts of A-(±)-N-{2-[4-(4-chlorophenyl)-4-hydroxy-3-methyl-1-piperidinyl]ethyl}-4-fluoro-2-nitrobenzamide hydrochloride in 160 parts of methanol is hydrogenated at normal pressure and at room temperature with 2 parts of Raney-nickel catalyst. After the calculated amount of hydrogen is taken up, the catalyst is filtered off and the filtrate is evaporated. The residue is converted into the hydrochloride salt in 2-propanone and 2-propanol. The salt is filtered off and crystallized from 2-propanol, yielding 1 part of A-(±)-2-amino-N-{2-[4-(4-chlorophenyl)-4-hydroxy-3-methyl-1-piperidinyl]ethyl}-4-fluorobenzamide dihydrochloride 2-propanolate; mp. 185° C.

EXAMPLE XCI

Following the procedure of Example XC and using therein A-(±)-N-{2-[4-(4-chlorophenyl)-4-hydroxy-3-methyl-1-piperidinyl]-ethyl}-2-nitrobenzamide as a starting material there is prepared:
A-(±)-2-amino-N--{-[4-(4-chlorophenyl)-4-hydroxy-3-methyl-1-piperidinyl]ethyl}benzamide dihydrochloride; mp. 190.5° C.

We claim:
1. A chemical compound selected from the group consisting of a N-[(1-piperidinyl)alkyl]arylcarboxamide derivative having the formula:

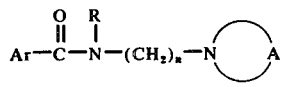

and the pharmaceutically acceptable acid addition salts thereof, wherein:

Ar is an aryl radical selected from the group consisting of phenyl, substituted phenyl, 2-thienyl, 2-furanyl, pyridinyl and 1-methyl-2-pyrrolyl, wherein said substituted phenyl is phenyl having from 1 to 3 substituents independently selected from the group consisting of halo, lower alkyl, lower alkyloxy, trifluoromethyl, nitro, hydroxy, amino, lower alkylcarbonyloxy and lower alkylcarbonylamino, provided that when more than 1 of said substituents are present only one thereof may be selected from the group consisting of hydroxy, amino, lower alkylcarbonyloxy and lower alkylcarbonylamino;

R is a member selected from the group consisting of hydrogen and lower alkyl;

n is an integer of from 2 to 3 inclusive; and

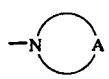

is a member selected from the group consisting of
a. a radical having the formula:

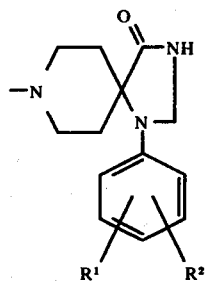

wherein $R^1$ and $R^2$ are each independently selected from the group consisting of hydrogen, halo, lower alkyl and trifluoromethyl;

b. a radical having the formula:

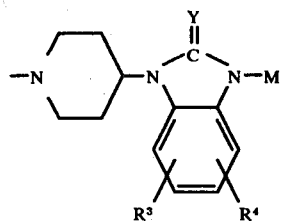

wherein $R^3$ and $R^4$ are each independently selected from the group consisting of hydrogen, halo, lower alkyl and trifluoromethyl; M is selected from the group consisting of hydrogen, lower alkyl, lower alkylcarbonyl and 2-cyanoethyl; Y is selected from the group consisting of O, S and lower alkylcarbonylimino; and the dotted line indicates that the double bond between the 3- and 4-carbon atoms of the piperidine nucleus is optional, provided that when there is a double bond between said 3- and 4-carbon atoms, then said Y is O and said M is hydrogen;

c. a radical having the formula:

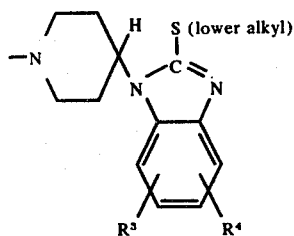

wherein R³ and R⁴ are each independently selected from the group consisting of hydrogen, halo, lower alkyl and trifluoromethyl; and d. a radical having the formula:

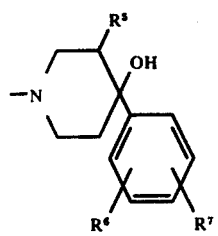

wherein R⁵ is selected from the group consisting of hydrogen and methyl; R⁶ is selected from the group consisting of hydrogen and halo; and R⁷ is selected from the group consisting of hydrogen, halo, lower alkyl and trifluoromethyl.

2. A chemical compound selected from the group consisting of 4-fluoro-N-{2-(4-fluorophenyl)-4-oxo-1,3,8-triazaspiro[4,5]dec-8-yl]ethyl}benzamide and the pharmaceutically acceptable acid addition salts thereof.

3. A chemical compound selected from the group consisting of 2-amino-4-fluoro-N-[2-(4-oxo-1-phenyl-1,3,8-triazaspiro[4,5]dec-8-yl)ethyl]benzamide and the pharmaceutically acceptable acid addition salts thereof.

4. A chemical compound selected from the group consisting of 2-chloro-N-{2-[1-(4-fluorophenyl)-4-oxo-1,3,8-triazaspiro[4,5]dec-8-yl]ethyl}benzamide and the pharmaceutically acceptable acid addition salts thereof.

5. A chemical compound selected from the group consisting of 2-chloro-4-fluoro-N-{2-[1-(4-fluorophenyl)-4-oxo-1,3,8-triazaspiro[4,5]dec-8-yl]ethyl} benzamide and the pharmaceutically acceptable acid addition salts thereof.

6. A chemical compound selected from the group consisting of N-{2-[4-(5-chloro-2,3-dihydro-2-oxo-1H-benzimidazol-1-yl)-1-piperidinyl]ethyl}-4-fluorobenzamide and the pharmaceutically accpetable acid addition salts thereof.

7. A chemical compound selected from the group consisting of 2-chloro-N-{2-[4-(5-chloro-2,3-dihydro-2-oxo-1H-benzimidazol-1-yl)-1-piperidinyl]ethyl}-4-fluorobenzamide and the pharmaceutically acceptable acid addition salts thereof.

8. A chemical compound selected from the group consisting of 2-amino-N-{2-[4-(2,3-dihydro-2-oxo-1H-benzimidazol-1-yl)-1-piperidinyl]ethyl}-4-fluorobenzamide and the pharmaceutically acceptable acid addition salts thereof.

9. A chemical compound having the formula:

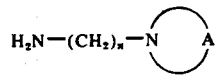

wherein the group

—N A in a member selected from the group consisting of:

a. a radical having the formula:

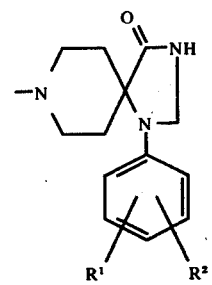

wherein R¹ and R² are each independently selected from the group consisting of hydrogen, halo, lower alkyl and trifluoromethyl;

b. a radical having the formula:

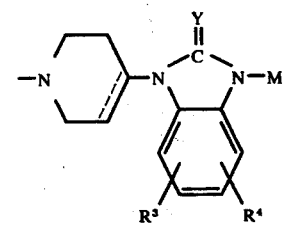

wherein R³ and R⁴ are each independently selected from the group consisting of hydrogen, halo, lower alkyl and trifluoromethyl; M is selected from the group consisting of hydrogen, lower alkyl, lower alkylcarbonyl and 2-cyanoethyl; Y is selected from the group consisting of O, S and lower alkylcarbonylimino; and the dotted line indicates that the double bond between the 3-and 4-carbon atoms of the piperidine nucleus is optional, provided that when there is a double bond between said 3-and 4-carbon atoms, then said Y is O and said M is hydrogen;

c. a radical having the formula:

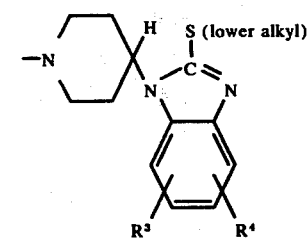

wherein R³ and R⁴ are each independently selected from the group consisting of hydrogen, halo, lower alkyl and trifluoromethyl; and d. a radical having the formula:

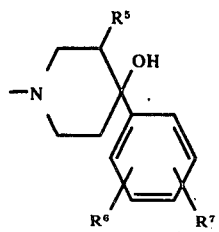

wherein $R^5$ is selected from the group consisting of hydrogen and methyl; $R^6$ is selected from the group consisting of hydrogen and halo; and $R^7$ is selected from the group consisting of hydrogen, halo, lower alkyl and trifluoromethyl.

10. A pharmaceutical composition in dosage unit form comprising per dosage unit an effective antiemetic or psychotropic amount of a compound selected from the group consisting of a N-[(1-piperidinyl)alkyl]arylcarboxamide derivative having the formula:

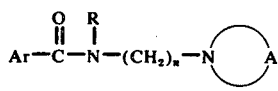

and the pharmaceutically acceptable acid salts thereof, wherein:

Ar is an aryl radical selected from the group consisting of phenyl, substituted phenyl, 2-thienyl, 2-furanyl, pyridinyl and 1-methyl-2-pyrrolyl, wherein said substituted phenyl is phenyl having from 1 to 3 substituents independently selected from the group consisting of halo, lower alkyl, lower alkyloxy, trifluoromethyl, nitro, hydroxy, amino, lower alkylcarbonyloxy and lower alkylcarbonylamino, provided that when more than 1 of said substituents are present only one thereof may be selected from the group consisting of hydroxy, amino, lower alkylcarbonyloxy and lower alkylcarbonylamino;

R is a member selected from the group consisting of hydrogen and lower alkyl;

n is an integer of from 2 to 3 inclusive; and

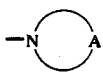

is a member selected from the group consisting of
a. a radical having the formula:

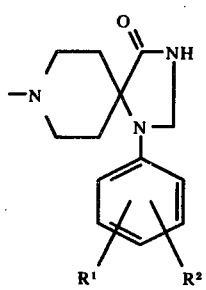

wherein $R^1$ and $R^2$ are each independently selected from the group consisting of hydrogen, halo, lower alkyl and trifluoromethyl;
b. a radical having the formula:

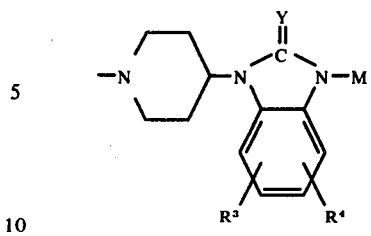

wherein $R^3$ and $R^4$ are each independently selected from the group consisting of hydrogen, halo, lower alkyl and trifluoromethyl; M is selected from the group consisting of hydrogen, lower alkyl, lower alkylcarbonyl and 2-cyanoethyl; Y is selected from the group consisting of O, S and lower alkylcarbonylimino; and the dotted line indicates that the double bond between the 3- and 4-carbon atoms of the piperidine nucleus is optional, provided that when there is a double bond between said 3- and 4-carbon atoms, then said Y is O and said M is hydrogen;

c. a radical having the formula:

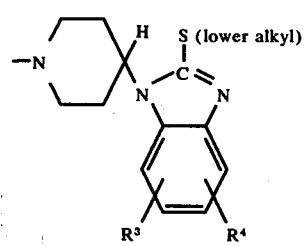

wherein $R^3$ and $R^4$ are each independently selected from the group consisting of hydrogen, halo, lower alkyl and trifluoromethyl; and d. a radical having the formula:

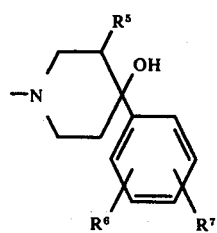

wherein $R^5$ is selected from the group consisting of hydrogen and methyl; $R^6$ is selected from the group consisting of hydrogen and halo; and $R^7$ is selected from the group consisting of hydrogen, halo, lower alkyl and trifluoromethyl;

in admixture with a pharmaceutical carrier.

11. The pharmaceutical composition of claim 10 wherein said pharmaceutical carrier is a solid, ingestible carrier.

12. The pharmaceutical composition of claim 10 wherein said pharmaceutical carrier is a liquid, ingestible carrier.

13. The pharmaceutical composition of claim 10 wherein said pharmaceutical carrier is a sterile liquid suitable for parenteral use.

14. A pharmaceutical composition in dosage unit form comprising per dosage unit an effective antiemetic or psychotropic amount of N-{2-[4-(5-chloro-2,3-dihydro-2-oxo-1H-benzimidazol-1yl)-1- piperidinyl]ethyl}-4-fluorobenzamide and the pharmaceutically acceptable acid addition salts thereof in admixture with a pharmaceutical carrier.

15. A method of inhibiting emesis or mental disorders which comprises the systemic administration to warm-blooded animals of an effective antimetic or psychotropic amount of a compound selected from the group consisting of a N-[(1-piperidinyl)alkyl]arylcarboxamide derivative having the formula:

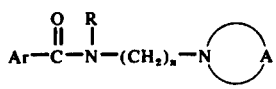

and the pharmaceutically acceptable acid addition salts thereof, wherein:

Ar is an aryl radical selected from the group consisting of phenyl, substituted phenyl, 2-thienyl, 2-furanyl, pyridinyl and 1-methyl-2-pyrrolyl, wherein said substituted phenyl is phenyl having from 1 to 3 substituents independently selected from the group consisting of halo, lower alkyl, lower alkyloxy, trifluoromethyl, nitro, hydroxy, amino, lower alkylcarbonyloxy and lower alkylcarbonylamino, provided that when more than 1 of said substituents are present only one thereof may be selected from the group consisting of hydroxy, amino, lower alkylcarbonyloxy and lower alkylcarbonylamino;

R is a member selected from the group consisting of hydrogen and lower alkyl;

n is an integer of from 2 to 3 inclusive; and the radical

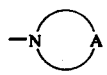

is a member selected from the group consisting of
a. a radical having the formula:

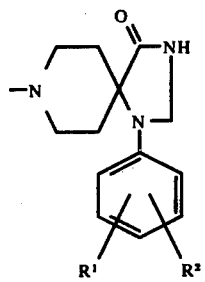

wherein $R^1$ and $R^2$ are each independently selected from the group consisting of hydrogen, halo, lower alkyl and trifluoromethyl;

b. a radical having the formula:

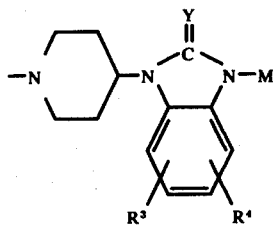

wherein $R^3$ and $R^4$ are each independently selected from the group consisting of hydrogen, halo, lower alkyl and trifluoromethyl; M is selected from the group consisting of hydrogen, lower alkyl, lower alkylcarbonyl and 2-cyanoethyl; Y is selected from the group consisting of O, S and lower alkylcarbonylimino; and the dotted line indicates that the double bond between the 3- and 4-carbon atoms of the piperidine nucleus is optional, provided that when there is a double bond between said 3- and 4-carbon atoms, then said Y is O and said M is hydrogen;

c. a radical having the formula:

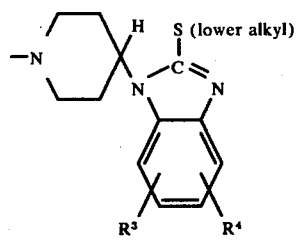

wherein $R^3$ and $R^4$ are each independently selected from the group consisting of hydrogen, halo, lower alkyl and trifluoromethyl; and d. a radical having the formula:

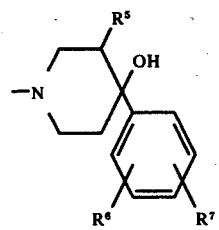

wherein $R^5$ is selected from the group consisting of hydrogen and methyl; $R^6$ is selected from the group consisting of hydrogen and halo; and $R^7$ is selected from the group consisting of hydrogen, halo, lower alkyl and trifluoromethyl;

in admixture with a pharmaceutical carrier.

16. A method of inhibiting emesis or mental disorders which comprises the systemic administration to warm-blooded animals of an effective antiemetic or psychotropic amount of N-{2-[4-(5-chloro-2,3-dihydro-2-oxo-1H-benzimidazol-1-yl)-1-piperidinyl]ethyl}-4-fluorobenzamide and the pharmaceutically acceptable acid addition salts thereof, in admixture with a pharmaceutical carrier.

* * * * *

UNITED STATES PATENT AND TRADEMARK OFFICE
CERTIFICATE OF CORRECTION

PATENT NO. : 4,031,226                             Page 1 of 2
DATED      : June 21, 1977
INVENTOR(S): Willem Soudijn; Ineke van Wijngaarden; Paul Adriaan Jan Janssen It is certified that error appears in the above-identified patent and that said Letters Patent are hereby corrected as shown below:

```
At Column 10, Line 31, "outline" should be -- outlined --.
At Column 19, Line 54, "metal" should be -- mental --.
At Column 22, Line 5,  "[4-chloro-2," should be -- [4-(5-chloro--.
At Column 22, Line 51, "...-lyl" should be -- -1-yl --.
At Column 23, Line 16, "propylen" should be -- propylene --.
At Column 25, Line 25, "an" should be -- and --.
At Column 25, Line 37, "4-nitro-n-2" should be
               -- 4-nitro-n-[2 --, and "triazasphiro" should be
               -- triazaspiro --.
At Column 27, Line 27, "an" should be -- and --.
At Column 28, Line 56, "yieldjg" should be -- yielding --.
At Column 29, Line 57, "1-(4-fluor" should be -- 1-(4-fluoro --.
At Column 32, Line 63, "fluorobenazmide" should be
               -- fluorobenzamide --.
At Column 33, Line 52, "6parts" should be -- 6 parts --.
At Column 36, Line 9, after "N,N-diethylethanamine" delete
               "," and add -- After the addition of another
               300 parts of trichloromethane, --.
At Column 38, Line 12-13, Delete "The organic layer is
               separated, diluted with 160 parts of water are
               added."
At Column 40, Line 25, "member" should be -- mixture --.
At Column 41, Line 37, after "{2[" delete "2-[."
At Column 41, Line 38, "[4,5[" should be -- [4,5] --.
At Column 42, Line 62, "226°C." should be -- 266°C. --.
At Column 44, Line 43, "element" should be -- eluent --.
At Column 45, Line 26, after "benzimidazol-" add -- 1- --.
At Column 45, Line 64, "1hydrogen" should be -- hydrogen --.
At Column 46, Line 3, "2,3-dihydro-2-oxo-" should be
               -- 2,3-dihydro-2-oxo-1H-benzimidazol --.
At Column 46, Line 68, "dired" should be -- dried --.
```

UNITED STATES PATENT AND TRADEMARK OFFICE
CERTIFICATE OF CORRECTION

PATENT NO. : 4,031,226
DATED : June 21, 1977
INVENTOR(S) : Willem Soudijn; Ineke van Wijngaarden; Paul Adriaan Jan Janssen It is certified that error appears in the above-identified patent and that said Letters Patent are hereby corrected as shown below:

At Column 47, Line 55, "{-[" should be -- {2-[ --.
At Column 49, Line 33, "-N-{2-(4-fluorophenyl)-4-oxo" should be -- N-{2-[1-(4-fluorophenyl)-4-oxo --.
At Column 49, Line 56, "accpetable" should be -- acceptable --.
At Column 51, Line 27, "acid salts" should be -- acid addition salts --.
At Column 53, Line 6, "antimetic" should be -- antiemetic --.

Signed and Sealed this

Twenty-first Day of November 1978

[SEAL]

Attest:

RUTH C. MASON
Attesting Officer

DONALD W. BANNER
Commissioner of Patents and Trademarks